(12) United States Patent
Tavernier et al.

(10) Patent No.: US 9,932,409 B2
(45) Date of Patent: Apr. 3, 2018

(54) TARGETED MODIFIED IL-1 FAMILY MEMBERS

(71) Applicants: VIB VZW, Ghent (BE); Universiteit Gent, Ghent (BE); Centre National De La Recherche Scientifique, Paris (FR); Universite Montpellier 2, Montpellier (FR); Centre Hospitalier Regional Universitaire de Montpellier, Montpellier (FR)

(72) Inventors: Jan Tavernier, Balegem (BE); Sarah Gerlo, Ghent (BE); Frank Peelman, Gentbrugge (BE); Gilles Uze, Montpellier (FR)

(73) Assignees: VIB VZW, Ghent (BE); UNIVERSITEIT GENT, Ghent (BE); CENTRE NATIONAL DE LA RECHERCHE SCIENTIFIQUE, Paris (FR); UNIVERSITÉMONTPELLIER 2, Montpellier (FR); CENTRE HOSPITALIER REGIONAL UNIVERSITAIRE DE MONTPELLIER, Montpellier (FR)

( * ) Notice: Subject to any disclaimer, the term of this patent is extended or adjusted under 35 U.S.C. 154(b) by 0 days.

(21) Appl. No.: 14/905,352

(22) PCT Filed: Jul. 4, 2014

(86) PCT No.: PCT/EP2014/064283
§ 371 (c)(1),
(2) Date: Jan. 15, 2016

(87) PCT Pub. No.: WO2015/007542
PCT Pub. Date: Jan. 22, 2015

(65) Prior Publication Data
US 2016/0152730 A1 Jun. 2, 2016

(30) Foreign Application Priority Data

Jul. 19, 2013 (EP) .................................. 13306047

(51) Int. Cl.
*C07K 16/00* (2006.01)
*C07K 14/00* (2006.01)
(Continued)

(52) U.S. Cl.
CPC ............ *C07K 16/40* (2013.01); *C07K 14/545* (2013.01); *C07K 16/2869* (2013.01);
(Continued)

(58) Field of Classification Search
CPC .. C07K 16/40; C07K 14/545; C07K 16/2869; C07K 16/32
See application file for complete search history.

(56) References Cited

U.S. PATENT DOCUMENTS 5,914,254 A 6/1999 Mascarenhas et al.
8,980,267 B2 3/2015 Grewal et al.
(Continued)

FOREIGN PATENT DOCUMENTS

WO 9102754 A1 3/1991
WO 2006053883 A1 5/2006
(Continued)

OTHER PUBLICATIONS

Garlanda et al., (Immunity. Dec. 12, 2013. 39(6):1003-1018).*
(Continued)

*Primary Examiner* — Cherie M Stanfield
(74) *Attorney, Agent, or Firm* — Morgan, Lewis & Bockius LLP

(57) ABSTRACT

The present disclosure relates to a modified Interleukin-1 (IL-1) family member cytokine, with reduced activity via its cytokine receptor, wherein said interleukin-1 family mem-
(Continued)

ber cytokine is specifically delivered to target cells. Preferably, the IL-1 family member cytokine is a mutant, more preferably it is a mutant IL-1 with low affinity to the IL-1 receptor, wherein said mutant IL-1 is specifically delivered to target cells. The targeting is preferably realized by fusion of the modified IL-1 family member cytokine to a targeting moiety, preferably an antibody or antibody-like molecule. The disclosure relates further to the use of such targeted modified IL-1 family member cytokine to treat diseases.

19 Claims, 7 Drawing Sheets

(51) Int. Cl.

| | |
|---|---|
| *A61K 38/00* | (2006.01) |
| *C07K 16/40* | (2006.01) |
| *C07K 14/545* | (2006.01) |
| *C07K 16/28* | (2006.01) |
| *C07K 16/32* | (2006.01) |
| *A61K 39/00* | (2006.01) |

(52) U.S. Cl.
CPC ........ *C07K 16/32* (2013.01); *A61K 2039/505* (2013.01); *C07K 2317/22* (2013.01); *C07K 2317/569* (2013.01); *C07K 2319/00* (2013.01)

(56) References Cited

U.S. PATENT DOCUMENTS

| | | | |
|---|---|---|---|
| 9,139,634 | B2 | 9/2015 | Morrison et al. |
| 2010/0172868 | A1 | 7/2010 | Morrison et al. |
| 2010/0297076 | A1 | 11/2010 | Morrison et al. |
| 2011/0104112 | A1 | 5/2011 | Morrison et al. |
| 2011/0274658 | A1 | 11/2011 | Silver et al. |
| 2013/0183298 | A1 | 7/2013 | Le et al. |
| 2015/0139951 | A1 | 5/2015 | Grewal et al. |

FOREIGN PATENT DOCUMENTS

| | | | | |
|---|---|---|---|---|
| WO | 2006115800 | A2 | 11/2006 | |
| WO | 2008014612 | A1 | 2/2008 | |
| WO | 2008124086 | A2 | 10/2008 | |
| WO | 2009003145 | A1 | 12/2008 | |
| WO | 2009039409 | A1 | 3/2009 | |
| WO | 2010036918 | A2 | 4/2010 | |
| WO | 2010066740 | A1 | 6/2010 | |
| WO | 2011020783 | A2 | 2/2011 | |
| WO | 2011029870 | A1 | 3/2011 | |
| WO | WO 2001029870 | A1 * | 3/2011 | ............ A61K 47/48 |
| WO | 2012170072 | A1 | 12/2012 | |
| WO | 2013059885 | A2 | 5/2013 | |
| WO | 2013107791 | A1 | 7/2013 | |
| WO | 2013134138 | A1 | 9/2013 | |

OTHER PUBLICATIONS

Wesolowski et al., "Single Domain Antibodies: Promising Experimental and Therapeutic Tools in Infection and Immunity", Med Microbial Immunol. 2009, vol. 198 pp. 157-174.
Deffar et al., "Nanobodies—The New Concept in Antibody Engineering" African Journal of Biotechnology, 2009, vol. 8 No. 12, pp. 2645-2652.
Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.
Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.
Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, (1993), pp. 8749-8757.
Coulstock, E., et al., "Liver-Targeting of Interferon-Alpha with Tissue Specific Domain Antibodies." PLOS ONE, vol. 8, No. 2, (2013), pp. 1-11.
de Bruyn, M., et al., "Antibody-Based Fusion Proteins to Target Death Receptors in Cancer", Cancer Letters, vol. 332, (2013), pp. 175-183.
Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garcin, G., et al., "High Efficiency Cell-Specific Targeting of Cytokine Activity", Nature Communications, (2014), pp. 1-9.
Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
International Search Report and Written Opinion in PCT/EP2013/050787, dated Jun. 14, 2013.
International Search Report and Written Opinion PCT/EP2014/063976, dated Oct. 29, 2014.
International Search Report and Written Opinion PCT/EP2014/064227, dated Feb. 5, 2015.
International Search Report and Written Opinion PCT/EP2014/064283, dated Oct. 1, 2014.
International Search Report and Written Opinion PCT/EP2014/065554, dated Oct. 30, 2014.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Masci, P. et al., "New and Modified Interferon alfas: Preclinical and Clinical Data", Current Oncology Reports, vol. 5, (2003), pp. 108-113.
Pan, M., et al., "Mutation of the IFNAR-1 Receptor Binding Site of Human IFN-[alpha]2 Generates Type I IFN competitive Antagonists", Biochemistry, vol. 47, (2008), pp. 12018-12027.
Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.
Rafei, M., et al., "A MCP1 Fusokine with CCR2-Specific Tumoricidal Activity", Molecular Cancer, vol. 10, No. 121, (2011), pp. 1-11.
Rafei, M., et al., "An Engineered GM-CSF-CCL2 Fusokine Is a Potent Inhibitor of CCR2-Driven Inflammation as Demonstrated in a Murine Model of Inflammatory Arthritis", The Journal of Immunology, vol. 183, (2009), pp. 1759-1766.
Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.
Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.
Schutyser, E., et al., "The CC Chemokine CCL20 and its Receptor CCR6", Cytokine & Growth Factor Reviews, vol. 14, (2003), pp. 409-426.
Weber, H., et al., "Single Amino Acid Changes that Render Human IFN-[alpha]2 Biologically Active on Mouse Cells", The EMBO Journal, vol. 6, No. 3, (1987), pp. 591-598.

(56) References Cited

OTHER PUBLICATIONS

Vaneycken, et al., "Preclinical Screening of Anti-HER2 Nanobodies for Molecular Imaging of Breast Cancer", The FASEB Journal, 2011, vol. 25, pp. 2433-2446.
Patris, et al., "Nanoimmunoassay onto a screen printed electrode for HER2 breast cancer biomarker determination", Talanta, 2014, vol. 130 pp. 164-170.

* cited by examiner

A.

B.

C.

D.

C. R120G/Q131G

D. R120G/H146A

```
                        SEQUENCE LISTING

<160> NUMBER OF SEQ ID NOS: 108

<210> SEQ ID NO 1
<211> LENGTH: 44
<212> TYPE: DNA
<213> ORGANISM: Artificial Sequence
<220> FEATURE:
<223> OTHER INFORMATION: Primer

<400> SEQUENCE: 1
ccgactacgc tggcggcagt gacggtgtca gaagcctgaa ctgc                    44

<210> SEQ ID NO 2
<211> LENGTH: 43
<212> TYPE: DNA
<213> ORGANISM: Artificial Sequence
<220> FEATURE:
<223> OTHER INFORMATION: Primer

<400> SEQUENCE: 2
ctggcggcag cgccctgtc gctagcctga actgcaccct gcg                     43

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
```
gcggcagcgc ccctgtcgga agcttgaact gcaccctgc                    39

<210> SEQ ID NO 4
<211> LENGTH: 52
<212> TYPE: DNA
<213> ORGANISM: Artificial Sequence
<220> FEATURE:
<223> OTHER INFORMATION: Primer

<400> SEQUENCE: 4
cgctggcggc agtgcccctg tcagaagcgc gaactgcacc ctgcgggaca gc      52

<210> SEQ ID NO 5
<211> LENGTH: 52
<212> TYPE: DNA
<213> ORGANISM: Artificial Sequence
<220> FEATURE:
<223> OTHER INFORMATION: Primer

<400> SEQUENCE: 5
cgcccctgtc agaagcctga actgcggcgg ccgggacagc cagcagaaaa gc      52

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
agaagcctga actgcacact gggggacagc cagcagaaaa gcctggtc           48

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ccctgcggga cagcgcgcag aaaagcctgg                              30

<210> SEQ ID NO 8
<211> LENGTH: 43
<212> TYPE: DNA
<213> ORGANISM: Artificial Sequence
<220> FEATURE:
<223> OTHER INFORMATION: Primer

<400> SEQUENCE: 8
ctgcaccctg cgggacagct ggcagaaaag cctggtcatg agc                43

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9
ctgcgggaca gccaggggaa gagcctggtc atgagcg                      37

<210> SEQ ID NO 10
<211> LENGTH: 45
<212> TYPE: DNA
<213> ORGANISM: Artificial Sequence

```
<220> FEATURE:
<223> OTHER INFORMATION: Primer

<400> SEQUENCE: 10
gcaccctgcg ggacagccag caggctagcc tggtcatgag cggcc          45

<210> SEQ ID NO 11
<211> LENGTH: 49
<212> TYPE: DNA
<213> ORGANISM: Artificial Sequence
<220> FEATURE:
<223> OTHER INFORMATION: Primer

<400> SEQUENCE: 11
cagcagaaaa gcctggtcat ggggtacccc tacgagctga aggcactgc       49

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
gcccctacga gctgaaggca ggtcatctgc agggccagga catgg           45

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
cgagctgaag gcactggctc ttcagggcca ggacatgg                  38

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
cctacgagct gaaggcactg ggtctgcagg gccaggacat gg              42

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gctgaaggca ctggagctgc agggccagg                            29

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
agctgaaggc actgaatctg cagggccag                            29
```

-continued

```
<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
ctgaaggcac tgcgtctgca gggccag                                        27

<210> SEQ ID NO 18
<211> LENGTH: 48
<212> TYPE: DNA
<213> ORGANISM: Artificial Sequence
<220> FEATURE:
<223> OTHER INFORMATION: Primer

<400> SEQUENCE: 18 gcggcccta cgagctgaag gcagcgcatg cgcagggcca ggacatgg                  48

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
ggcactgcat ctggagggcc aggacat                                        27

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
gaaggcactg catctgggtg gccaggacat ggaacagc                            38

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gcactgcatc tgctgggcca ggacatg                                        27

<210> SEQ ID NO 22
<211> LENGTH: 47
<212> TYPE: DNA
<213> ORGANISM: Artificial Sequence
<220> FEATURE:
<223> OTHER INFORMATION: Primer

<400> SEQUENCE: 22
cgagctgaag gcactgcatc tgggggcgg ggacatggaa cagcagg                   47

<210> SEQ ID NO 23
<211> LENGTH: 48
<212> TYPE: DNA
<213> ORGANISM: Artificial Sequence
<220> FEATURE:
<223> OTHER INFORMATION: Primer
```

```
<400> SEQUENCE: 23
gcactgcatc tgcagggcgg ggccatggaa cagcaggtcg tgttcagc                    48

<210> SEQ ID NO 24
<211> LENGTH: 54
<212> TYPE: DNA
<213> ORGANISM: Artificial Sequence
<220> FEATURE:
<223> OTHER INFORMATION: Primer

<400> SEQUENCE: 24
gcactgcatc tgcagggcca ggacggggaa cagcaggtgg tgttcagcat gagc            54

<210> SEQ ID NO 25
<211> LENGTH: 58
<212> TYPE: DNA
<213> ORGANISM: Artificial Sequence
<220> FEATURE:
<223> OTHER INFORMATION: Primer

<400> SEQUENCE: 25
catggaacag caggtggtgt tcagcatgag cgccgtgcag ggcgaggaaa gcaacgac        58

<210> SEQ ID NO 26
<211> LENGTH: 56
<212> TYPE: DNA
<213> ORGANISM: Artificial Sequence
<220> FEATURE:
<223> OTHER INFORMATION: Primer

<400> SEQUENCE: 26
gcaggtcgtg ttcagcatga gcgccgtgga gggcgaggaa agcaatgaca agatcc         56

<210> SEQ ID NO 27
<211> LENGTH: 46
<212> TYPE: DNA
<213> ORGANISM: Artificial Sequence
<220> FEATURE:
<223> OTHER INFORMATION: Primer

<400> SEQUENCE: 27
ccgacttcac catgcaggcc gtctccagcg gcggcagcag atctgg                     46

<210> SEQ ID NO 28
<211> LENGTH: 50
<212> TYPE: DNA
<213> ORGANISM: Artificial Sequence
<220> FEATURE:
<223> OTHER INFORMATION: Primer

<400> SEQUENCE: 28
gcatgagctt cgtgggggc aaggaaagca atgacaagat ccccgtggcc                  50

<210> SEQ ID NO 29
<211> LENGTH: 55
<212> TYPE: DNA
<213> ORGANISM: Artificial Sequence
<220> FEATURE:
<223> OTHER INFORMATION: Primer

<400> SEQUENCE: 29
gcagggcgag gaaagcggcg gcaagatccc cgtggcccta ggcctgaaag agaag          55

<210> SEQ ID NO 30
```

```
<211> LENGTH: 32
<212> TYPE: DNA
<213> ORGANISM: Artificial Sequence
<220> FEATURE:
<223> OTHER INFORMATION: Primer

<400> SEQUENCE: 30
gaaagcaacg acaaggcccc cgtggccctg gg                           32

<210> SEQ ID NO 31
<211> LENGTH: 36
<212> TYPE: DNA
<213> ORGANISM: Artificial Sequence
<220> FEATURE:
<223> OTHER INFORMATION: Primer

<400> SEQUENCE: 31
gcaacgacaa gatccccgcg gccctgggcc tgaaag                       36

<210> SEQ ID NO 32
<211> LENGTH: 55
<212> TYPE: DNA
<213> ORGANISM: Artificial Sequence
<220> FEATURE:
<223> OTHER INFORMATION: Primer

<400> SEQUENCE: 32
gcagctggaa agcgtggatc ccaagaacta ccccgagaaa aagatggaaa aacgc   55

<210> SEQ ID NO 33
<211> LENGTH: 49
<212> TYPE: DNA
<213> ORGANISM: Artificial Sequence
<220> FEATURE:
<223> OTHER INFORMATION: Primer

<400> SEQUENCE: 33
ccccaagaac taccccaagg caaagatgga aaagcgcttc gtgttcaac          49

<210> SEQ ID NO 34
<211> LENGTH: 55
<212> TYPE: DNA
<213> ORGANISM: Artificial Sequence
<220> FEATURE:
<223> OTHER INFORMATION: Primer

<400> SEQUENCE: 34
gcagctggaa agcgtggatc ccaagaacta ccccaaggac aagatggaaa aacgc   55

<210> SEQ ID NO 35
<211> LENGTH: 46
<212> TYPE: DNA
<213> ORGANISM: Artificial Sequence
<220> FEATURE:
<223> OTHER INFORMATION: Primer

<400> SEQUENCE: 35
ccccaagaac taccccaagg cagcgatgga aaaacgcttc gtgttc             46

<210> SEQ ID NO 36
<211> LENGTH: 44
<212> TYPE: DNA
<213> ORGANISM: Artificial Sequence
<220> FEATURE:
<223> OTHER INFORMATION: Primer

<400> SEQUENCE: 36
```
aaaaacgctt cgtgttcaac agcatcgaga tcaacaacaa gctc         44

<210> SEQ ID NO 37
<211> LENGTH: 41
<212> TYPE: DNA
<213> ORGANISM: Artificial Sequence
<220> FEATURE:
<223> OTHER INFORMATION: Primer

<400> SEQUENCE: 37
aaaaacgctt cgtgttcaac cagatcgaga tcaacaacaa g            41

<210> SEQ ID NO 38
<211> LENGTH: 42
<212> TYPE: DNA
<213> ORGANISM: Artificial Sequence
<220> FEATURE:
<223> OTHER INFORMATION: Primer

<400> SEQUENCE: 38
gcttcgtgtt caacaagatc tcgatcaaca acaagctcga gt           42

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
cttcgtgttc aacaagatca agatcaacaa caagctcga               39

<210> SEQ ID NO 40
<211> LENGTH: 53
<212> TYPE: DNA
<213> ORGANISM: Artificial Sequence
<220> FEATURE:
<223> OTHER INFORMATION: Primer

<400> SEQUENCE: 40
ggaaaaacgc ttcgtcttca acagcatctc gatcaacaac aagctcgagt tcg   53

<210> SEQ ID NO 41
<211> LENGTH: 48
<212> TYPE: DNA
<213> ORGANISM: Artificial Sequence
<220> FEATURE:
<223> OTHER INFORMATION: Primer

<400> SEQUENCE: 41
cgcttcgtgt tcaacaagat ctcgatcaac gccaagctcg agttcgag     48

<210> SEQ ID NO 42
<211> LENGTH: 46
<212> TYPE: DNA
<213> ORGANISM: Artificial Sequence
<220> FEATURE:
<223> OTHER INFORMATION: Primer

<400> SEQUENCE: 42
caacaagatc gagatcaaca gcagcctcga attcgagagc gcccag       46

<210> SEQ ID NO 43
<211> LENGTH: 50
<212> TYPE: DNA

<213> ORGANISM: Artificial Sequence
<220> FEATURE:
<223> OTHER INFORMATION: Primer

<400> SEQUENCE: 43
ccccaactgg tacatcagta ctagtcaggc caagaatatg cccgtgttcc            50

<210> SEQ ID NO 44
<211> LENGTH: 46
<212> TYPE: DNA
<213> ORGANISM: Artificial Sequence
<220> FEATURE:
<223> OTHER INFORMATION: Primer

<400> SEQUENCE: 44
cagcactagt caggccgagc agatgcccgt cttcctgggc ggcacc                46

<210> SEQ ID NO 45
<211> LENGTH: 49
<212> TYPE: DNA
<213> ORGANISM: Artificial Sequence
<220> FEATURE:
<223> OTHER INFORMATION: Primer

<400> SEQUENCE: 45
catcagcact agtcaggcca agcagatgcc cgtcttcctg ggcggcacc              49

<210> SEQ ID NO 46
<211> LENGTH: 39
<212> TYPE: DNA
<213> ORGANISM: Artificial Sequence
<220> FEATURE:
<223> OTHER INFORMATION: Primer

<400> SEQUENCE: 46
gcggcagcgc ccctgtcgga agcttgaact gcaccctgc                        39

<210> SEQ ID NO 47
<211> LENGTH: 38
<212> TYPE: DNA
<213> ORGANISM: Artificial Sequence
<220> FEATURE:
<223> OTHER INFORMATION: Primer

<400> SEQUENCE: 47
cgagctgaag gcactggctc ttcagggcca ggacatgg                         38

<210> SEQ ID NO 48
<211> LENGTH: 48
<212> TYPE: DNA
<213> ORGANISM: Artificial Sequence
<220> FEATURE:
<223> OTHER INFORMATION: Primer

<400> SEQUENCE: 48
gcggccccta cgagctgaag gcagcgcatg cgcagggcca ggacatgg              48

<210> SEQ ID NO 49
<211> LENGTH: 39
<212> TYPE: DNA
<213> ORGANISM: Artificial Sequence
<220> FEATURE:
<223> OTHER INFORMATION: Primer

<400> SEQUENCE: 49
gcggcagcgc ccctgtcgga agcttgaact gcaccctgc                        39

<210> SEQ ID NO 50
<211> LENGTH: 56
<212> TYPE: DNA
<213> ORGANISM: Artificial Sequence
<220> FEATURE:
<223> OTHER INFORMATION: Primer

<400> SEQUENCE: 50
gcaggtcgtg ttcagcatga gcgccgtgga gggcgaggaa agcaatgaca agatcc      56

<210> SEQ ID NO 51
<211> LENGTH: 55
<212> TYPE: DNA
<213> ORGANISM: Artificial Sequence
<220> FEATURE:
<223> OTHER INFORMATION: Primer

<400> SEQUENCE: 51
gcagctggaa agcgtggatc ccaagaacta ccccgagaaa aagatggaaa aacgc       55

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
ctgcgggaca gccaggggaa gagcctggtc atgagcg                           37

<210> SEQ ID NO 53
<211> LENGTH: 56
<212> TYPE: DNA
<213> ORGANISM: Artificial Sequence
<220> FEATURE:
<223> OTHER INFORMATION: Primer

<400> SEQUENCE: 53
gcaggtcgtg ttcagcatga gcgccgtgga gggcgaggaa agcaatgaca agatcc      56

<210> SEQ ID NO 54
<211> LENGTH: 55
<212> TYPE: DNA
<213> ORGANISM: Artificial Sequence
<220> FEATURE:
<223> OTHER INFORMATION: Primer

<400> SEQUENCE: 54
gcagctggaa agcgtggatc ccaagaacta ccccgagaaa aagatggaaa aacgc       55

<210> SEQ ID NO 55
<211> LENGTH: 44
<212> TYPE: DNA
<213> ORGANISM: Artificial Sequence
<220> FEATURE:
<223> OTHER INFORMATION: Primer

<400> SEQUENCE: 55
gcagttcagg cttctgacac cgtcactgcc gccagcgtag tcgg                   44

<210> SEQ ID NO 56
<211> LENGTH: 43
<212> TYPE: DNA
<213> ORGANISM: Artificial Sequence
<220> FEATURE:

<223> OTHER INFORMATION: Primer

<400> SEQUENCE: 56
cgcagggtgc agttcaggct agcgacaggg gcgctgccgc cag        43

<210> SEQ ID NO 57
<211> LENGTH: 39
<212> TYPE: DNA
<213> ORGANISM: Artificial Sequence
<220> FEATURE:
<223> OTHER INFORMATION: Primer

<400> SEQUENCE: 57
gcagggtgca gttcaagctt ccgacagggg cgctgccgc        39

<210> SEQ ID NO 58
<211> LENGTH: 52
<212> TYPE: DNA
<213> ORGANISM: Artificial Sequence
<220> FEATURE:
<223> OTHER INFORMATION: Primer

<400> SEQUENCE: 58
gctgtcccgc agggtgcagt tcgcgcttct gacaggggca ctgccgccag cg        52

<210> SEQ ID NO 59
<211> LENGTH: 52
<212> TYPE: DNA
<213> ORGANISM: Artificial Sequence
<220> FEATURE:
<223> OTHER INFORMATION: Primer

<400> SEQUENCE: 59
gcttttctgc tggctgtccc ggccgccgca gttcaggctt ctgacagggg cg        52

<210> SEQ ID NO 60
<211> LENGTH: 48
<212> TYPE: DNA
<213> ORGANISM: Artificial Sequence
<220> FEATURE:
<223> OTHER INFORMATION: Primer

<400> SEQUENCE: 60
gaccaggctt ttctgctggc tgtcccccag tgtgcagttc aggcttct        48

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
ccaggctttt ctgcgcgctg tcccgcaggg        30

<210> SEQ ID NO 62
<211> LENGTH: 43
<212> TYPE: DNA
<213> ORGANISM: Artificial Sequence
<220> FEATURE:
<223> OTHER INFORMATION: Primer

<400> SEQUENCE: 62
gctcatgacc aggcttttct gccagctgtc ccgcagggtg cag        43

<210> SEQ ID NO 63
<211> LENGTH: 37
<212> TYPE: DNA
<213> ORGANISM: Artificial Sequence
<220> FEATURE:
<223> OTHER INFORMATION: Primer

<400> SEQUENCE: 63
cgctcatgac caggctcttc ccctggctgt cccgcag                               37

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
ggccgctcat gaccaggcta gcctgctggc tgtcccgcag ggtgc                      45

<210> SEQ ID NO 65
<211> LENGTH: 49
<212> TYPE: DNA
<213> ORGANISM: Artificial Sequence
<220> FEATURE:
<223> OTHER INFORMATION: Primer

<400> SEQUENCE: 65
gcagtgcctt cagctcgtag gggtacccca tgaccaggct tttctgctg                  49

<210> SEQ ID NO 66
<211> LENGTH: 45
<212> TYPE: DNA
<213> ORGANISM: Artificial Sequence
<220> FEATURE:
<223> OTHER INFORMATION: Primer

<400> SEQUENCE: 66
ccatgtcctg gccctgcaga tgacctgcct tcagctcgta ggggc                      45

<210> SEQ ID NO 67
<211> LENGTH: 38
<212> TYPE: DNA
<213> ORGANISM: Artificial Sequence
<220> FEATURE:
<223> OTHER INFORMATION: Primer

<400> SEQUENCE: 67
ccatgtcctg gccctgaaga gccagtgcct tcagctcg                              38

<210> SEQ ID NO 68
<211> LENGTH: 42
<212> TYPE: DNA
<213> ORGANISM: Artificial Sequence
<220> FEATURE:
<223> OTHER INFORMATION: Primer

<400> SEQUENCE: 68
ccatgtcctg gccctgcaga cccagtgcct tcagctcgta gg                         42

<210> SEQ ID NO 69
<211> LENGTH: 29
<212> TYPE: DNA
<213> ORGANISM: Artificial Sequence
<220> FEATURE:
<223> OTHER INFORMATION: Primer

```
<400> SEQUENCE: 69
cctggccctg cagctccagt gccttcagc                                          29

<210> SEQ ID NO 70
<211> LENGTH: 29
<212> TYPE: DNA
<213> ORGANISM: Artificial Sequence
<220> FEATURE:
<223> OTHER INFORMATION: Primer

<400> SEQUENCE: 70
ctggccctgc agattcagtg ccttcagct                                          29

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
ctggccctgc agacgcagtg ccttcag                                            27

<210> SEQ ID NO 72
<211> LENGTH: 48
<212> TYPE: DNA
<213> ORGANISM: Artificial Sequence
<220> FEATURE:
<223> OTHER INFORMATION: Primer

<400> SEQUENCE: 72
ccatgtcctg gccctgcgca tgcgctgcct tcagctcgta ggggccgc                     48

<210> SEQ ID NO 73
<211> LENGTH: 27
<212> TYPE: DNA
<213> ORGANISM: Artificial Sequence
<220> FEATURE:
<223> OTHER INFORMATION: Primer

<400> SEQUENCE: 73
atgtcctggc cctccagatg cagtgcc                                            27

<210> SEQ ID NO 74
<211> LENGTH: 38
<212> TYPE: DNA
<213> ORGANISM: Artificial Sequence
<220> FEATURE:
<223> OTHER INFORMATION: Primer

<400> SEQUENCE: 74
gctgttccat gtcctggcca cccagatgca gtgccttc                                38

<210> SEQ ID NO 75
<211> LENGTH: 27
<212> TYPE: DNA
<213> ORGANISM: Artificial Sequence
<220> FEATURE:
<223> OTHER INFORMATION: Primer

<400> SEQUENCE: 75
catgtcctgg cccagcagat gcagtgc                                            27

<210> SEQ ID NO 76
<211> LENGTH: 47
```

-continued

<212> TYPE: DNA
<213> ORGANISM: Artificial Sequence
<220> FEATURE:
<223> OTHER INFORMATION: Primer

<400> SEQUENCE: 76
cctgctgttc catgtccccg cccccagat gcagtgcctt cagctcg        47

<210> SEQ ID NO 77
<211> LENGTH: 48
<212> TYPE: DNA
<213> ORGANISM: Artificial Sequence
<220> FEATURE:
<223> OTHER INFORMATION: Primer

<400> SEQUENCE: 77
gctgaacacg acctgctgtt ccatggcccc gccctgcaga tgcagtgc        48

<210> SEQ ID NO 78
<211> LENGTH: 54
<212> TYPE: DNA
<213> ORGANISM: Artificial Sequence
<220> FEATURE:
<223> OTHER INFORMATION: Primer

<400> SEQUENCE: 78
gctcatgctg aacaccacct gctgttcccc gtcctggccc tgcagatgca gtgc        54

<210> SEQ ID NO 79
<211> LENGTH: 58
<212> TYPE: DNA
<213> ORGANISM: Artificial Sequence
<220> FEATURE:
<223> OTHER INFORMATION: Primer

<400> SEQUENCE: 79
gtcgttgctt tcctcgccct gcacggcgct catgctgaac accacctgct gttccatg        58

<210> SEQ ID NO 80
<211> LENGTH: 56
<212> TYPE: DNA
<213> ORGANISM: Artificial Sequence
<220> FEATURE:
<223> OTHER INFORMATION: Primer

<400> SEQUENCE: 80
ggatcttgtc attgctttcc tcgccctcca cggcgctcat gctgaacacg acctgc        56

<210> SEQ ID NO 81
<211> LENGTH: 46
<212> TYPE: DNA
<213> ORGANISM: Artificial Sequence
<220> FEATURE:
<223> OTHER INFORMATION: Primer

<400> SEQUENCE: 81
ccagatctgc tgccgccgct ggagacggcc tgcatggtga agtcgg        46

<210> SEQ ID NO 82
<211> LENGTH: 50
<212> TYPE: DNA
<213> ORGANISM: Artificial Sequence
<220> FEATURE:
<223> OTHER INFORMATION: Primer

<400> SEQUENCE: 82

```
ggccacgggg atcttgtcat tgctttcctt gcccccacg aagctcatgc               50
```

<210> SEQ ID NO 83
<211> LENGTH: 55
<212> TYPE: DNA
<213> ORGANISM: Artificial Sequence
<220> FEATURE:
<223> OTHER INFORMATION: Primer

<400> SEQUENCE: 83

```
cttctctttc aggcctaggg ccacggggat cttgccgccg ctttcctcgc cctgc         55
```

<210> SEQ ID NO 84
<211> LENGTH: 32
<212> TYPE: DNA
<213> ORGANISM: Artificial Sequence
<220> FEATURE:
<223> OTHER INFORMATION: Primer

<400> SEQUENCE: 84

```
cccagggcca cgggggcctt gtcgttgctt tc                                  32
```

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85

```
ctttcaggcc cagggccgcg gggatcttgt cgttgc                              36
```

<210> SEQ ID NO 86
<211> LENGTH: 55
<212> TYPE: DNA
<213> ORGANISM: Artificial Sequence
<220> FEATURE:
<223> OTHER INFORMATION: Primer

<400> SEQUENCE: 86

```
gcgttttttcc atcttttttct cggggtagtt cttgggatcc acgctttcca gctgc        55
```

<210> SEQ ID NO 87
<211> LENGTH: 49
<212> TYPE: DNA
<213> ORGANISM: Artificial Sequence
<220> FEATURE:
<223> OTHER INFORMATION: Primer

<400> SEQUENCE: 87

```
gttgaacacg aagcgctttt ccatctttgc cttggggtag ttcttgggg               49
```

<210> SEQ ID NO 88
<211> LENGTH: 55
<212> TYPE: DNA
<213> ORGANISM: Artificial Sequence
<220> FEATURE:
<223> OTHER INFORMATION: Primer

<400> SEQUENCE: 88

```
gcgttttttcc atcttgtcct tggggtagtt cttgggatcc acgctttcca gctgc         55
```

<210> SEQ ID NO 89
<211> LENGTH: 46
<212> TYPE: DNA
<213> ORGANISM: Artificial Sequence

```
<220> FEATURE:
<223> OTHER INFORMATION: Primer

<400> SEQUENCE: 89
gaacacgaag cgttttccca tcgctgcctt ggggtagttc ttgggg                46

<210> SEQ ID NO 90
<211> LENGTH: 44
<212> TYPE: DNA
<213> ORGANISM: Artificial Sequence
<220> FEATURE:
<223> OTHER INFORMATION: Primer

<400> SEQUENCE: 90
gagcttgttg ttgatctcga tgctgttgaa cacgaagcgt tttt                  44

<210> SEQ ID NO 91
<211> LENGTH: 41
<212> TYPE: DNA
<213> ORGANISM: Artificial Sequence
<220> FEATURE:
<223> OTHER INFORMATION: Primer

<400> SEQUENCE: 91
cttgttgttg atctcgatct ggttgaacac gaagcgtttt t                     41

<210> SEQ ID NO 92
<211> LENGTH: 42
<212> TYPE: DNA
<213> ORGANISM: Artificial Sequence
<220> FEATURE:
<223> OTHER INFORMATION: Primer

<400> SEQUENCE: 92
actcgagctt gttgttgatc gagatcttgt tgaacacgaa gc                    42

<210> SEQ ID NO 93
<211> LENGTH: 39
<212> TYPE: DNA
<213> ORGANISM: Artificial Sequence
<220> FEATURE:
<223> OTHER INFORMATION: Primer

<400> SEQUENCE: 93
tcgagcttgt tgttgatctt gatcttgttg aacacgaag                        39

<210> SEQ ID NO 94
<211> LENGTH: 53
<212> TYPE: DNA
<213> ORGANISM: Artificial Sequence
<220> FEATURE:
<223> OTHER INFORMATION: Primer

<400> SEQUENCE: 94
cgaactcgag cttgttgttg atcgagatgc tgttgaagac gaagcgtttt tcc        53

<210> SEQ ID NO 95
<211> LENGTH: 48
<212> TYPE: DNA
<213> ORGANISM: Artificial Sequence
<220> FEATURE:
<223> OTHER INFORMATION: Primer

<400> SEQUENCE: 95
ctcgaactcg agcttggcgt tgatcgagat cttgttgaac acgaagcg              48
```

<210> SEQ ID NO 96
<211> LENGTH: 46
<212> TYPE: DNA
<213> ORGANISM: Artificial Sequence
<220> FEATURE:
<223> OTHER INFORMATION: Primer

<400> SEQUENCE: 96
ctgggcgctc tcgaattcga ggctgctgtt gatctcgatc ttgttg        46

<210> SEQ ID NO 97
<211> LENGTH: 50
<212> TYPE: DNA
<213> ORGANISM: Artificial Sequence
<220> FEATURE:
<223> OTHER INFORMATION: Primer

<400> SEQUENCE: 97
ggaacacggg catattcttg gcctgactag tactgatgta ccagttgggg        50

<210> SEQ ID NO 98
<211> LENGTH: 46
<212> TYPE: DNA
<213> ORGANISM: Artificial Sequence
<220> FEATURE:
<223> OTHER INFORMATION: Primer

<400> SEQUENCE: 98
ggtgccgccc aggaagacgg gcatctgctc ggcctgacta gtgctg        46

<210> SEQ ID NO 99
<211> LENGTH: 49
<212> TYPE: DNA
<213> ORGANISM: Artificial Sequence
<220> FEATURE:
<223> OTHER INFORMATION: Primer

<400> SEQUENCE: 99
ggtgccgccc aggaagacgg gcatctgctt ggcctgacta gtgctgatg        49

<210> SEQ ID NO 100
<211> LENGTH: 39
<212> TYPE: DNA
<213> ORGANISM: Artificial Sequence
<220> FEATURE:
<223> OTHER INFORMATION: Primer

<400> SEQUENCE: 100
gcagggtgca gttcaagctt ccgacagggg cgctgccgc        39

<210> SEQ ID NO 101
<211> LENGTH: 38
<212> TYPE: DNA
<213> ORGANISM: Artificial Sequence
<220> FEATURE:
<223> OTHER INFORMATION: Primer

<400> SEQUENCE: 101
ccatgtcctg gccctgaaga gccagtgcct tcagctcg        38

<210> SEQ ID NO 102
<211> LENGTH: 48
<212> TYPE: DNA
<213> ORGANISM: Artificial Sequence
<220> FEATURE:
<223> OTHER INFORMATION: Primer -continued

<400> SEQUENCE: 102
ccatgtcctg gccctgcgca tgcgctgcct tcagctcgta ggggccgc        48

<210> SEQ ID NO 103
<211> LENGTH: 39
<212> TYPE: DNA
<213> ORGANISM: Artificial Sequence
<220> FEATURE:
<223> OTHER INFORMATION: Primer

<400> SEQUENCE: 103
gcagggtgca gttcaagctt ccgacagggg cgctgccgc        39

<210> SEQ ID NO 104
<211> LENGTH: 56
<212> TYPE: DNA
<213> ORGANISM: Artificial Sequence
<220> FEATURE:
<223> OTHER INFORMATION: Primer

<400> SEQUENCE: 104
ggatcttgtc attgctttcc tcgccctcca cggcgctcat gctgaacacg acctgc        56

<210> SEQ ID NO 105
<211> LENGTH: 55
<212> TYPE: DNA
<213> ORGANISM: Artificial Sequence
<220> FEATURE:
<223> OTHER INFORMATION: Primer

<400> SEQUENCE: 105 gcgttttttcc atctttttct cggggtagtt cttgggatcc acgctttcca gctgc        55

<210> SEQ ID NO 106
<211> LENGTH: 37
<212> TYPE: DNA
<213> ORGANISM: Artificial Sequence
<220> FEATURE:
<223> OTHER INFORMATION: Primer

<400> SEQUENCE: 106
cgctcatgac caggctcttc ccctggctgt cccgcag        37

<210> SEQ ID NO 107
<211> LENGTH: 56
<212> TYPE: DNA
<213> ORGANISM: Artificial Sequence
<220> FEATURE:
<223> OTHER INFORMATION: Primer

<400> SEQUENCE: 107
ggatcttgtc attgctttcc tcgccctcca cggcgctcat gctgaacacg acctgc        56

<210> SEQ ID NO 108
<211> LENGTH: 55
<212> TYPE: DNA
<213> ORGANISM: Artificial Sequence
<220> FEATURE:
<223> OTHER INFORMATION: Primer

<400> SEQUENCE: 108 gcgttttttcc atctttttct cggggtagtt cttgggatcc acgctttcca gctgc        55

TARGETED MODIFIED IL-1 FAMILY MEMBERS

The present invention relates to a modified Interleukin-1 (IL-1) family member cytokine, with reduced activity via its cytokine receptor, wherein said Interleukin-1 family member cytokine is specifically delivered to target cells. Preferably, the IL-1 family member cytokine is a mutant, more preferably it is a mutant IL-1 with low affinity to the IL-1 receptor, wherein said mutant IL-1 is specifically delivered to target cells. The targeting is preferably realized by fusion of the modified IL-1 family member cytokine to a targeting moiety, preferably an antibody or antibody-like molecule. The invention relates further to the use of such targeted modified IL-1 family member cytokine to treat diseases.

The Interleukin-1 (IL-1) family consists of 11 structurally related family members (IL-1α, IL-1-β, IL-1Ra, IL-18, IL-33 and IL-1F5 to IL-1F10), that are among the most potent immune system signaling molecules, acting through a group of closely related receptors. All IL-1 receptors have a similar mode of activation: upon binding of ligand to the primary receptor subunit (i.e. IL-1R1 for IL-1α and β, IL-18R for IL-18 and ST2 for IL-33), a second receptor subunit is recruited (i.e. IL-1RAP for IL-1α and β, IL-18RAP for IL-18 and IL-1RAP for IL-33) and signalling is initiated via juxtaposition of the receptor subunits' cytoplasmic Toll/IL-1 receptor (TIR) domains. The dimerized TIR domains provide a docking platform for the MYD88 adaptor protein, which via recruitment of other intermediates leads to activation of the pro-inflammatory nuclear factor-κB (NF-κB) and mitogen-activated protein kinase (MAPK) pathways. The IL-1 family members are primarily produced by innate immune cells and act on a variety of cell types during the immune response (for review see Sims and Smith, 2010).

T lymphocytes are one of the main IL-1 family target cells and the potentiating effects of in particular IL-1α and IL-1β on the expansion and differentiation of different T cell subsets, in particular CD8+ T cells (Ben-Sasson, 2011; Ben-Sasson, 2013) and Th17 cells (Sutton et al., 2006; Acosta-Rodriguez et al., 2007; Dunne et al., 2010; Shaw et al., 2012) have been firmly established. Th17 cells are characterized by the production of IL-17 and play an important role in auto-immune disease and chronic inflammation (reviewed in Wilke et al., 2011). Among T cell subsets, Th17 cells express the highest levels of the IL-1R and IL-1 plays an important role in Th17 priming.

IL-18 is best known as an IFNγ-inducing cytokine with a potent action on Th1 cells and natural killer (NK) cells, on (Okamura et al., 1995; Takeda et al. 1998). In addition, IL-18 enhances neutrophil function (Leung et al., 2001). Several reports demonstrate IL-18 anti-tumour action in animal models (Micallef et al., 1997; Loeffler et al., 2008; Wigginton et al., 2002; Zaki et al., 2010) and recombinant human IL-18 therapy recently entered clinical trials to evaluate its efficacy for treatment of advanced cancer (Robertson et al., 2008). As opposed to IL-18, IL-33 acts primarily on Th2 cells (Schmitz et al., 2005) and mast cells (Allakhverdi et al., 2007), and recently was shown to act on CD8+ T cells to drive antiviral responses (Bonilla et al., 2012). The other IL-1 family members are less well characterized, but in summary different IL-1 family members have specificities for different T-cell subsets or other cell types and hence have different therapeutic applications.

Besides having indirect anti-tumour activity, via activation of T and NK cells, IL-1 family members were shown to have direct cytostatic properties, which were most convincingly demonstrated on human melanoma cells (Morinaga et al., 1990; Usui et al., 1991; Rangnekar et al., 1992).

In view of the contribution of several IL-1 family members to inflammatory processes, clinical interest has been mainly oriented towards the development of IL-1-antagonizing strategies (Dinarello et al., 2012). Nevertheless, exploitation of controlled agonistic IL-1 activity could have applications in different physiological/pathological processes, where immunostimulatory effects would be desirable. One of the main concerns regarding the use of IL-1 in immunostimulatory therapies, is its severe toxicity when administered systemically. However, when IL-1 action could be confined to a selected cellular population, the toxicity issue might be resolved, which opens up therapeutic perspectives.

For instance, although there has been a lot of interest on blocking Th17 responses in view of their pathogenic role in auto-immune conditions such as multiple sclerosis, rheumatoid arthritis and inflammatory bowel disease (Wilke et al., 2011), normal Th17 function is indispensable for protective immunity against a range of pathogens, including *Mycobacterium tuberculosis* (Khader et al., 2007), *Klebsiella pneumoniae* (Ye et al., 2001) and *Bordetella pertussis* (Higgins et al., 2006). As IL-1β stimulates Th17 function, the idea has been raised to use IL-1β as a T-cell adjuvant to enhance the response to weak vaccines (Ben-Sasson et al., 2011). Other applications could be the targeting of IL-1β or IL-33 to the CD8+ T-cell population to enhance antiviral responses or targeting IL-18 to Th1 cells or NK cells to promote anti-tumor activity.

Surprisingly we found that it is possible to design IL-1 family modifications that are defective in activating their receptor, but, when fused to a targeting moiety, regain their activity on selected cell types by a concentration effect at the cell surface. The IL-1 mutants have a reduced affinity for their cognate receptors, and hence are unable to efficiently bind and activate their receptors. However, by fusing them to a targeting moiety (such as a nanobody) the activity of the mutant IL-1 family member is restored on cells expressing the cell surface target, recognized by the targeting moiety. Because the activation is confined to the selected targeted cell types only, no major systemic toxicity occurs.

A first aspect of the invention is a targeting construct, comprising a modified IL-1 family member cytokine, characterized by a reduced affinity for its cytokine receptor, and a targeting moiety. IL-1 family member cytokines are known to the person skilled in the art, and include, but are not limited to IL-1α, IL-1β, IL-1Ra, IL18, IL-36Ra, IL-36α, IL-37, IL-36β, IL-36γ, IL-38 and IL-33 (also indicated as IL-1F1, IL-1F2, IL-1F3, IL-1F4, IL-1F5, IL-1F6, IL-1F7, IL-1F8, IL-1F9, IL-1F10 and IL-1F11, respectively). For a review on the IL-1 family, see Dinarello (2011). A modified IL-1 family cytokine means that the IL-1 family cytokine has been changed to alter the affinity to its receptor, with as final result that the modified IL-1 family cytokine has a reduced affinity for the receptor and a consequent reduced biological activity, as compared to the endogenous wild type cytokine that binds normally to the receptor. Such a modification can be a modification that decreases the activity of the normal wild type cytokine, or it can be a modification that increases the affinity of a homologous, non-endogenous IL-1 family cytokine (such as, but not limited to a IL-1 family cytokine of another species that is not active on a human IL-1 family cytokine receptor). Modifications can be any modification reducing or increasing the activity, known to the person skilled in the art, including but not limited to chemical and/or enzymatic modifications such as pegylation and glycosylation, fusion to other proteins and mutations. Preferably said modification is a mutation, even more preferably it is a mutation decreasing the affinity of the IL-1 family cytokine. A reduced affinity and a consequent reduced biological activity as used here means that the modified IL-1 family cytokine has a biological activity of less than 70% of the biological activity of the IL-1 family cytokine, even more preferably less than 60% of the biological activity of the IL-1 family cytokine, more preferably less than 50% of the biological activity of the IL-1 family cytokine, more preferably less than 40% of the biological activity of the IL-1 family cytokine, more preferably less than 30% of the biological activity of the IL-1 family cytokine, more preferably less than 20% of the biological activity of the IL-1 family cytokine, more preferably less than 10% of the biological activity of the IL-1 family cytokine, most preferably less than 1% of the biological activity of the IL-1 family cytokine as compared to the IL-1 family cytokine that normally binds to the receptor. Preferably, the modified IL-1 family cytokine is a mutant of the wild type IL-1 family cytokine and the activity is compared with the wild type IL-1 family cytokine. The affinity and/or the activity can be measured by any method known to the person skilled in the art.

A preferred embodiment of the invention is a targeting construct, comprising a mutant IL-1β characterized by reduced affinity for the Interleukin-1 receptor type I (IL-1RI) and/or the interleukin-1 receptor accessory protein (IL-1 RAcP) receptor, and a targeting moiety. A mutant IL-1β as used here can be any mutant form that has a lower affinity for the receptor and as a consequence a reduced activation of the proinflammatory transcription factor NFκB. The affinity of the mutant IL-1β to the receptor, in comparison to the affinity of the wild type IL-1β to the receptor can be measured by Scatchard plot analysis and computer-fitting of binding data (e.g. Scatchard, 1949) or by reflectometric interference spectroscopy under flow through conditions, as described by Brecht et al. (1993). The activity of the mutant IL-1β is typically measured using a bioassay (for example by the induction of cell death) or by measuring signaling events downstream of the receptor. Such signaling events can be the modification or nuclear translocation of NF-κB, or the induction of a selected reporter gene. The mutant may be a point mutant, a deletion or an insertion mutant, or a combination thereof; several mutations may be present in one protein. Preferably, said mutant IL-1β is obtained by active mutagenesis, such as, but not limited to site directed mutagenesis by polymerase chain reaction amplification. Preferably, said mutant IL-1β has a biological activity of less than 70% of the biological activity of the wild type IL-1β, even more preferably less than 60% of the biological activity of the wild type IL-1β, more preferably less than 50% of the biological activity of the wild IL-1β, more preferably less than 40% of the biological activity of the wild IL-1β, more preferably less than 30% of the biological activity of the wild IL-1β, more preferably less than 20% of the biological activity of the wild IL-1β, more preferably less than 10% of the biological activity of the wild type, most preferably less than 1% of the wild type of which it is deduced (i.e. the wild type IL-1β of which the coding sequence has been mutated to obtain the mutant IL-1β) Preferably, said mutant is a mutant selected from the group consisting of A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, I172A, V174A, K208E, K209X, K209A/K210A, K219X, E221X, E221S/N224A, N224S/K225S, E244K, N245Q (wherein X can be any change in amino acid, preferably a non-conservative change). Even more preferably said mutation is selected from the group consisting of R120A, R120G, Q130A, Q130W, H146A, H146G, H146E, H146N, H146R, Q148E, Q148G, Q148L, K209A, K209D, K219S, K219Q, E221S and E221K. Most preferably said mutation is selected from the group consisting of R120G, H146N, H146R, Q148E, Q148G and K209A. (numbering base on the human IL-1β sequence, genbank accession number NP_000567, version NP-000567.1, GI: 10835145).

Preferred regions for mutations for IL-18 are Y37-K44, R49-Q54, D59-R63, E67-C74, R80, M87-A97, N127-K129, Q139-M149, K165-K171, R183 and Q190-N191. Most preferred are the regions E67-C74 and M87-A97 (numbering based on the human sequence, genbank accession number AAV38697, version AAV38697.1, GI: 54696650).

Preferred regions for mutations for IL-33 are I113-Y122, S127-E139, E144-D157, Y163-M183, E200, Q215, L220-C227 and T260-E269 (numbering based on the human sequence, genbank accession number NP_254274, version NP_254274.1, GI:15559209)

Preferably, said targeting moiety is targeting to a marker expressed on an IL-1β receptor expressing cell, preferably a cell expressing IL1-RI. In one preferred embodiment, said targeting moiety is directed to a tissue specific marker.

The modified IL-1 family member is linked to a targeting moiety. "Linked" as used here may be by a covalent binding, or it may be by an affinity binding. A "targeting moiety" as used here is a binding molecule that can direct the fusion protein towards a binding site on a cell that is expressing a receptor for the IL-1 family member, by specific interaction between the binding site and the binding molecule. In one preferred embodiment, said binding molecule is a small compound, specifically binding to a molecule situated on the outside of the cell. In another preferred embodiment, said molecule is a sugar structure, directed towards a lectin-like molecule expressed on the cell wall. In another preferred embodiment said binding molecule is a peptide, targeting the tumor or inflammation environment. Such peptides are known to the person skilled in the art, and include, but are not limited to NGR and RGD peptides (Yang et al., 2011; WO2005054293). In still another preferred embodiment, said binding molecule is a protein comprising a binding domain. This includes, but is not limited to carbohydrate binding domains (CBD) (Blake et al, 2006), lectin binding proteins, heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO2010066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009). Preferably, said targeting moiety consists of a single polypeptide chain and is not post-translationally modified. Even more preferably, said targeting moiety is a nanobody.

The targeting moiety can be any targeting moiety known to the person skilled in the art. In a non-limiting example, said targeting moiety may be a bispecific antibody, directed to a binding site on the target cell for one specificity, and to the targeted cytokine, or to a tag fused to said cytokine for the other specificity. In another non-limiting example, the targeting moiety may be chemically linked to the mutant Interleukin-1, or it may be a recombinant fusion protein. Preferably, said targeting construct is a recombinant fusion protein. The targeting moiety may be fused directly to the mutant IL-1β, or it may be fused with the help of a linker fragment, preferably a GGS linker. The targeting moiety may be fused at the aminoterminal or at the carboxyterminal end of the mutated IL-1β; preferably said targeting moiety is fused at the carboxyterminal extremity of the mutated IL-1β molecule. The targeting construct may further comprise other domains such as, but not limited to a tag sequence, a signal sequence, another cytokine or an antibody.

Another aspect of the invention is a targeting construct according to the invention for use as a medicament. One preferred embodiment is a targeting construct according to the invention for use in stimulation of the immune response. Indeed, it is know that IL-1 treatment can induce antigen expression on B-cells (Killer et al., 1989); likewise, IL-18 treatment is augmenting cellular and humoral immunities (Kinoshita et al., 2011). In a similar way, it has been demonstrated that IL-1 acts on T-cells to enhance the magnitude of in vivo immune responses (Ben-Sasson et al., 2011; Ben Sasson et al., 2013). Therefore, one preferred aspect of the invention is the targeting construct according to the invention for use as an adjuvant in vaccination. The targeting construct according to the invention is especially interesting in this respect, as the pro-inflammatory effect of normal wild type IL-1 makes the application of IL-1 as such impossible.

Still another aspect of the invention is a targeting construct according to the invention for use in treatment of cancer. Indeed, Morinaga et al., 1990, Usui et al., 1991 and Rangnekar et al., 1992 have shown that IL-1 family members do have direct cytostatic properties, which were most convincingly demonstrated on human melanoma cells.

EXAMPLES

Materials and Methods to the Examples

Cloning of IL-1-Nanobody Fusion Proteins.

Figure 1:
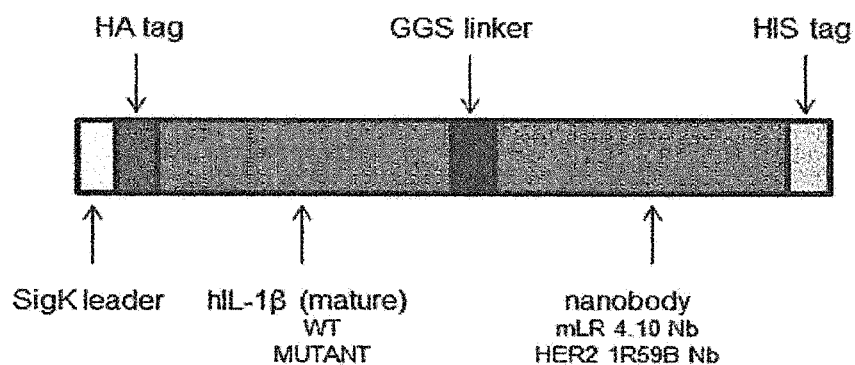
FIG. 1: Schematic representation of the IL-1β-nanobody fusion proteins

The 4-10 nanobody directed against the murine leptin receptor is described in Zabeau et al. (2012) and in the patent WO 2006/053883. The anti-Her2 nanobody 1R59B is described in Vaneycken et al. (2011). Both nanobodies were cloned with a C-terminal His tag in the pMET7 eukaryotic expression vector. A codon-optimized sequence encoding the mature IL-1β protein, preceded by the SigK leader peptide, and equipped with an N-terminal HA tag, was generated via gene synthesis (Invitrogen Gene Art). To generate the IL-1β-nanobody fusion proteins, the IL-1β sequence was cloned 5' to the nanobody sequence in pMet7, with a 13×GGS linker separating the cytokine and nanobody moieties. (FIG. 1)

IL-1β Mutants.

IL-1β mutants expected to have reduced binding affinity for the IL-1R were selected based on literature and analysis of published crystal structures of human IL-1β complexed with its receptor. Mutations in the hIL-1β moiety were created via site-directed mutagenesis (QuickChange, Stratagene) using the mutagenesis primers as indicated in table I:

TABLE I mutants and primers used

| | | Fw primer | Rev primer |
|---|---|---|---|
| 1 | A117G/ P118G | CCGACTACGCTGGCGGCAGTGACGGTGTCA GAAGCCTGAACTGC | GCAGTTCAGGCTTCTGACACCGTCACTG CCGCCAGCGTAGTCGG |
| 2 | R120A | CTGGCGGCAGCGCCCCTGTCGCTAGCCTGA ACTGCACCCTGCG | CGCAGGGTGCAGTTCAGGCTAGCGACA GGGGCGCTGCCGCCAG |
| 3 | R120G | GCGGCAGCGCCCCTGTCGGAAGCTTGAACT GCACCCTGC | GCAGGGTGCAGTTCAAGCTTCCGACAG GGGCGCTGCCGC |
| 4 | L122A | CGCTGGCGGCAGTGCCCCTGTCAGAAGCGC GAACTGCACCCTGCGGGACAGC | GCTGTCCCGCAGGGTGCAGTTCGCGCT TCTGACAGGGGCACTGCCGCCAGCG |
| 5 | T125G/ L126G | CGCCCCTGTCAGAAGCCTGAACTGCGGCGG CCGGGACAGCCAGCAGAAAAGC | GCTTTTCTGCTGGCTGTCCCGGCCGCC GCAGTTCAGGCTTCTGACAGGGGCG |
| 6 | R127G | AGAAGCCTGAACTGCACACTGGGGGACAGC CAGCAGAAAAGCCTGGTC | GACCAGGCTTTTCTGCTGGCTGTCCCCC AGTGTGCAGTTCAGGCTTCT |
| 7 | Q130A | CCCTGCGGGACAGCGCGCAGAAAAGCCTGG | CCAGGCTTTTCTGCGCGCTGTCCCGCA GGG |
| 8 | Q130W | CTGCACCCTGCGGGACAGCTGGCAGAAAAG CCTGGTCATGAGC | GCTCATGACCAGGCTTTTCTGCCAGCTG TCCCGCAGGGTGCAG |

TABLE I-continued mutants and primers used

| | | Fw primer | Rev primer |
|---|---|---|---|
| 9 | Q131G | CTGCGGGACAGCCAGGGGAAGAGCCTGGTC ATGAGCG | CGCTCATGACCAGGCTCTTCCCCTGGCT GTCCCGCAG |
| 10 | K132A | GCACCCTGCGGGACAGCCAGCAGGCTAGCC TGGTCATGAGCGGCC | GGCCGCTCATGACCAGGCTAGCCTGCT GGCTGTCCCGCAGGGTGC |
| 11 | S137G/ Q138Y | CAGCAGAAAAGCCTGGTCATGGGGTACCCCT ACGAGCTGAAGGCACTGC | GCAGTGCCTTCAGCTCGTAGGGGTACC CCATGACCAGGCTTTTCTGCTG |
| 12 | L145G | GCCCCTACGAGCTGAAGGCAGGTCATCTGCA GGGCCAGGACATGG | CCATGTCCTGGCCCTGCAGATGACCTG CCTTCAGCTCGTAGGGGC |
| 13 | H146A | CGAGCTGAAGGCACTGGCTCTTCAGGGCCA GGACATGG | CCATGTCCTGGCCCTGAAGAGCCAGTG CCTTCAGCTCG |
| 14 | H146G | CCTACGAGCTGAAGGCACTGGGTCTGCAGG GCCAGGACATGG | CCATGTCCTGGCCCTGCAGACCCAGTG CCTTCAGCTCGTAGG |
| 15 | H146E | GCTGAAGGCACTGGAGCTGCAGGGCCAGG | CCTGGCCCTGCAGCTCCAGTGCCTTCA GC |
| 16 | H146N | AGCTGAAGGCACTGAATCTGCAGGGCCAG | CTGGCCCTGCAGATTCAGTGCCTTCAGCT |
| 17 | H146R | CTGAAGGCACTGCGTCTGCAGGGCCAG | CTGGCCCTGCAGACGCAGTGCCTTCAG |
| 18 | L145A/ L147A | GCGGCCCCTACGAGCTGAAGGCAGCGCATG CGCAGGGCCAGGACATGG | CCATGTCCTGGCCCTGCGCATGCGCTG CCTTCAGCTCGTAGGGGCCGC |
| 19 | Q148E | GGCACTGCATCTGGAGGGCCAGGACAT | ATGTCCTGGCCCTCCAGATGCAGTGCC |
| 20 | Q148G | GAAGGCACTGCATCTGGGTGGCCAGGACAT GGAACAGC | GCTGTTCCATGTCCTGGCCACCCAGATG CAGTGCCTTC |
| 21 | Q148L | GCACTGCATCTGCTGGGCCAGGACATG | CATGTCCTGGCCCAGCAGATGCAGTGC |
| 22 | Q148G/ Q150G | CGAGCTGAAGGCACTGCATCTGGGGGGCGG GGACATGGAACAGCAGG | CCTGCTGTTCCATGTCCCCGCCCCCCA GATGCAGTGCCTTCAGCTCG |
| 23 | Q150G/ D151A | GCACTGCATCTGCAGGGCGGGGCCATGGAA CAGCAGGTCGTGTTCAGC | GCTGAACACGACCTGCTGTTCCATGGCC CCGCCCTGCAGATGCAGTGC |
| 24 | M152G | GCACTGCATCTGCAGGGCCAGGACGGGGAA CAGCAGGTGGTGTTCAGCATGAGC | GCTCATGCTGAACACCACCTGCTGTTCC CCGTCCTGGCCCTGCAGATGCAGTGC |
| 25 | F162A | CATGGAACAGCAGGTGGTGTTCAGCATGAGC GCCGTGCAGGGCGAGGAAAGCAACGAC | GTCGTTGCTTTCCTCGCCCTGCACGGC GCTCATGCTGAACACCACCTGCTGTTCC ATG |
| 26 | F162A/ Q164E | GCAGGTCGTGTTCAGCATGAGCGCCGTGGA GGGCGAGGAAAGCAATGACAAGATCC | GGATCTTGTCATTGCTTTCCTCGCCCTC CACGGCGCTCATGCTGAACACGACCTGC |
| 27 | F166A | CCGACTTCACCATGCAGGCCGTCTCCAGCGG CGGCAGCAGATCTGG | CCAGATCTGCTGCCGCCGCTGGAGACG GCCTGCATGGTGAAGTCGG |
| 28 | Q164E/ E167K | GCATGAGCTTCGTGGGGGGCAAGGAAAGCA ATGACAAGATCCCCGTGGCC | GGCCACGGGGATCTTGTCATTGCTTTCC TTGCCCCCCACGAAGCTCATGC |
| 29 | N169G/ D170G | GCAGGGCGAGGAAAGCGGCGGCAAGATCCC CGTGGCCCTAGGCCTGAAAGAGAAG | CTTCTCTTTCAGGCCTAGGGCCACGGG GATCTTGCCGCCGCTTTCCTCGCCCTGC |
| 30 | I172A | GAAAGCAACGACAAGGCCCCCGTGGCCCTG GG | CCCAGGGCCACGGGGGCCTTGTCGTTG CTTTC |
| 31 | V174A | GCAACGACAAGATCCCCGCGGCCCTGGGCC TGAAAG | CTTTCAGGCCCAGGGCCGCGGGGATCT TGTCGTTGC |
| 32 | K208E | GCAGCTGGAAAGCGTGGATCCCAAGAACTAC CCCGAGAAAAAGATGGAAAAACGC | GCGTTTTTCCATCTTTTTCTCGGGGTAGT TCTTGGGATCCACGCTTTCCAGCTGC |
| 33 | K209A | CCCCAAGAACTACCCCAAGGCAAAGATGGAA AAGCGCTTCGTGTTCAAC | GTTGAACACGAAGCGCTTTTCCATCTTT GCCTTGGGGTAGTTCTTGGGG |
| 34 | K209D | GCAGCTGGAAAGCGTGGATCCCAAGAACTAC CCCAAGGACAAGATGGAAAAACGC | GCGTTTTTCCATCTTGTCCTTGGGGTAG TTCTTGGGATCCACGCTTTCCAGCTGC |

TABLE I-continued mutants and primers used

| | | Fw primer | Rev primer |
|---|---|---|---|
| 35 | K209A/ K210A | CCCCAAGAACTACCCCAAGGCAGCGATGGAA AAACGCTTCGTGTTC | GAACACGAAGCGTTTTTCCATCGCTGCC TTGGGGTAGTTCTTGGGG |
| 36 | K219S | AAAAACGCTTCGTGTTCAACAGCATCGAGAT CAACAACAAGCTC | GAGCTTGTTGTTGATCTCGATGCTGTTG AACACGAAGCGTTTTT |
| 37 | K219Q | AAAAACGCTTCGTGTTCAACCAGATCGAGAT CAACAACAAG | CTTGTTGTTGATCTCGATCTGGTTGAAC ACGAAGCGTTTTT |
| 38 | E221S | GCTTCGTGTTCAACAAGATCTCGATCAACAAC AAGCTCGAGT | ACTCGAGCTTGTTGTTGATCGAGATCTT GTTGAACACGAAGC |
| 39 | E221K | CTTCGTGTTCAACAAGATCAAGATCAACAACA AGCTCGA | TCGAGCTTGTTGTTGATCTTGATCTTGTT GAACACGAAG |
| 40 | K219S/ E221S | GGAAAAACGCTTCGTCTTCAACAGCATCTCG ATCAACAACAAGCTCGAGTTCG | CGAACTCGAGCTTGTTGTTGATCGAGAT GCTGTTGAAGACGAAGCGTTTTTCC |
| 41 | E221S/ N224A | CGCTTCGTGTTCAACAAGATCTCGATCAACG CCAAGCTCGAGTTCGAG | CTCGAACTCGAGCTTGGCGTTGATCGAG ATCTTGTTGAACACGAAGCG |
| 42 | N224S/ K225S | CAACAAGATCGAGATCAACAGCAGCCTCGAA TTCGAGAGCGCCCAG | CTGGGCGCTCTCGAATTCGAGGCTGCT GTTGATCTCGATCTTGTTG |
| 43 | E244K | CCCCAACTGGTACATCAGTACTAGTCAGGCC AAGAATATGCCCGTGTTCC | GGAACACGGGCATATTCTTGGCCTGACT AGTACTGATGTACCAGTTGGGG |
| 44 | N245Q | CAGCACTAGTCAGGCCGAGCAGATGCCCGT CTTCCTGGGCGGCACC | GGTGCCGCCCAGGAAGACGGGCATCTG CTCGGCCTGACTAGTGCTG |
| 45 | E244K/ N245Q | CATCAGCACTAGTCAGGCCAAGCAGATGCCC GTCTTCCTGGGCGGCACC | GGTGCCGCCCAGGAAGACGGGCATCTG CTTGGCCTGACTAGTGCTGATG |
| 46* | R120G/ Q131G | GCGGCAGCGCCCCTGTCGGAAGCTTGAACT GCACCCTGC | GCAGGGTGCAGTTCAAGCTTCCGACAG GGGCGCTGCCGC |
| 47* | R120G/ H146A | CGAGCTGAAGGCACTGGCTCTTCAGGGCCA GGACATGG | CCATGTCCTGGCCCTGAAGAGCCAGTG CCTTCAGCTCG |
| 49* | R120G/ L145A/ L147A | GCGGCCCCTACGAGCTGAAGGCAGCGCATG CGCAGGGCCAGGACATGG | CCATGTCCTGGCCCTGCGCATGCGCTG CCTTCAGCTCGTAGGGGCCGC |
| 48** | R120G/ Q148G | GCGGCAGCGCCCCTGTCGGAAGCTTGAACT GCACCCTGC | GCAGGGTGCAGTTCAAGCTTCCGACAG GGGCGCTGCCGC |
| 50* | R120G/ F162A/ Q164E | GCAGGTCGTGTTCAGCATGAGCGCCGTGGA GGGCGAGGAAAGCAATGACAAGATCC | GGATCTTGTCATTGCTTTCCTCGCCCTC CACGGCGCTCATGCTGAACACGACCTGC |
| 51* | R120G/ K208E | GCAGCTGGAAAGCGTGGATCCCAAGAACTAC CCCGAGAAAAAGATGGAAAAACGC | GCGTTTTTCCATCTTTTTCTCGGGGTAGT TCTTGGGATCCACGCTTTCCAGCTGC |
| 52** | Q131G/ Q148G | CTGCGGGACAGCCAGGGGAAGAGCCTGGTC ATGAGCG | CGCTCATGACCAGGCTCTTCCCCTGGCT GTCCCGCAG |
| 53** | Q148G/ F162A/ Q164E | GCAGGTCGTGTTCAGCATGAGCGCCGTGGA GGGCGAGGAAAGCAATGACAAGATCC | GGATCTTGTCATTGCTTTCCTCGCCCTC CACGGCGCTCATGCTGAACACGACCTGC |
| 54** | Q148G/ K208E | GCAGCTGGAAAGCGTGGATCCCAAGAACTAC CCCGAGAAAAAGATGGAAAAACGC | GCGTTTTTCCATCTTTTTCTCGGGGTAGT TCTTGGGATCCACGCTTTCCAGCTGC |

*double/triple-mutants were created using R120G as template.
**double/triple-mutants were created using Q148G as template.

Production of IL-1β Fusion Proteins.

IL-1β fusion proteins were produced in HEK293T cells. For small-scale production, HEK293T cells were seeded in 6-well plates at 400000 cells/well in DMEM supplemented with 10% FCS. After 24 hours, culture medium was replaced by medium with reduced serum (DMEM/5% FCS) and cells were transfected using linear PEI. Briefly, PEI transfection mix was prepared by combining 1 μg expression vector with 5 μg PEI in 160 μl DMEM, incubated for 10 minutes at RT and added to the wells dropwise. After 24 hours, transfected cells were washed with DMEM and layered with 1.5 ml OptiMem/well for protein production. Conditioned media were recuperated after 48 hours, filtered through 0.45μ filters and stored at −20° C. IL-1β content in the conditioned media was determined by Elisa according to the manufacturer's instructions (R&D Systems).

NF-κB Reporter Gene Assay.

To assess IL-1R activation, we used HEK-Blue™ IL-1β cells that stably express the IL-1R (Invivogen) and transfected them transiently with an NF-κB luciferase reporter-gene. Briefly, HEK-Blue™ IL-1β cells were seeded in culture medium (DMEM/10% FCS) in 96-well plates (10000 cells/well) and transfected the next day using the calciumphosphate precipitation method with the indicated amounts of expression plasmids and 5 ng/well of the 3κB-Luc reportergene plasmid (Vanden Berghe et al., 1998). 24 hours post-transfection, culture medium was replaced by starvation medium (DMEM) and 48 hours post-transfection, cells were induced for 6 hours with fusion proteins. After induction, cells were lysed and luciferase activity in lysates was determined using the Promega Firefly Luciferase Assay System on a Berthold centro LB960 luminometer.

Analysis of NF-κB Nuclear Translocation Via Confocal Microscopy.

For confocal imaging, $10^5$ HEK293-T cells/well (in 6-well plate) were seeded on glass coverslips (Zeiss), coated with poly-L-lysine (Sigma). The next day, cells were transfected with 200 ng/well of empty vector or HER2Δcyt expression plasmid using the calcium phosphate precipitation method. After 48 hours, cells were treated for 30 minutes with vehicle (medium) or IL1-Her2 nanobody fusion protein (10 ng/ml). Next, cells were rinsed with 1×PBS and fixed for 15 minutes at room temperature in 4% paraformaldehyde. After three washes with 1×PBS, cells were permeabilized with 0.1% Triton X-100 in 1×PBS for 10 minutes and blocked in 1% BSA in 1×PBS for another 10 minutes at room temperature. Samples were then incubated for 1 hour at 37° C. with rabbit anti-p65 antibody (Santa Cruz C20, diluted 1:800) and mouse anti-Flag Antibody (Sigma M2, 1:2000). After four washes in 1×PBS, cells were incubated for 1 hour at room temperature with anti-rabbit Alexa 488 and anti-mouse Alexa 594 fluorochrome-conjugated secondary antibodies (both diluted 1:800). After secondary antibody incubation, cells were washed four times in 1×PBS and nuclei were stained with DAPI (2 µg/ml). After a final wash step in 1×PBS, coverslips were mounted using propyl gallate. Images were acquired using a 60× 1.35 NA objective on an Olympus IX-81 laser scanning confocal microscope and analyzed using Fluoview 1000 software.

Example 1: IL-1β-Ligand and IL-1β-Nanobody Fusion Proteins

FIG. 1 shows a scheme of the IL-1β-nanobody fusion proteins constructed with either WT hIL-1β or the hIL1β mutants described in table I.

Figure 2:
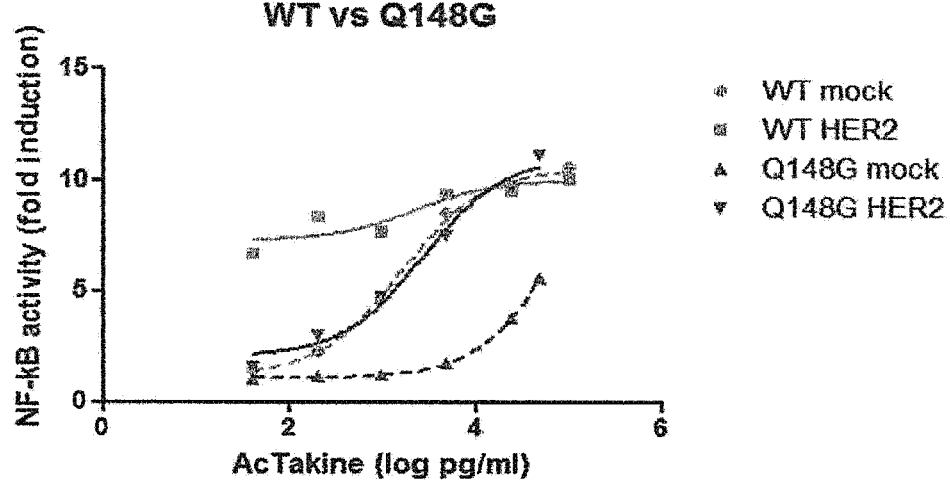
FIGS. 2A-G: Concentration dependency of the induction of the NFκB activity by wild type and mutant Q148G IL-1 Her2 nanobody fusions (FIG. 2A) and other selected mutants (FIGS. 2B-G), in mock transfected cells, or cells transfected with signaling deficient Her2.
Figure 2:
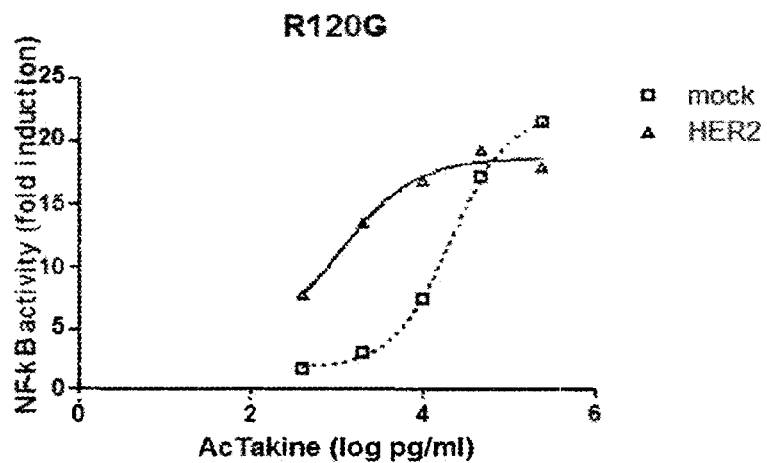
Figure 2:
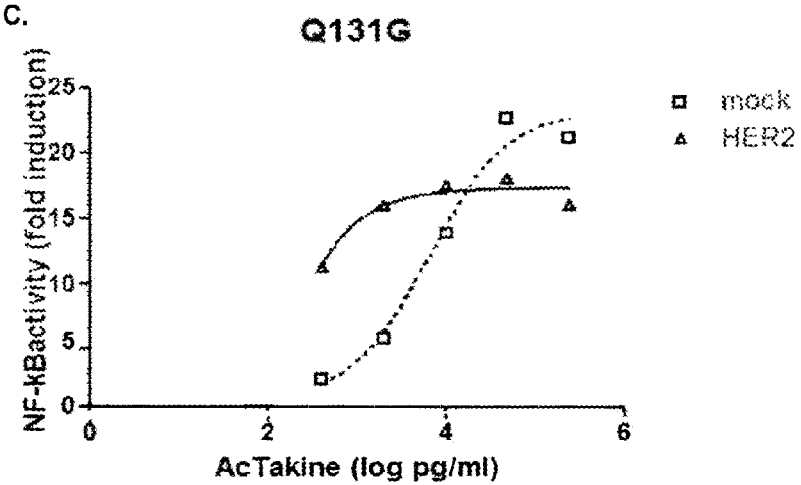
Figure 2:
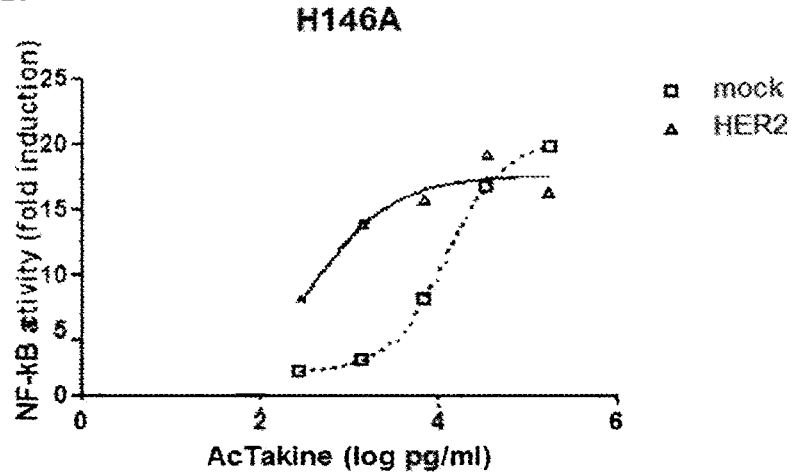
Figure 2:
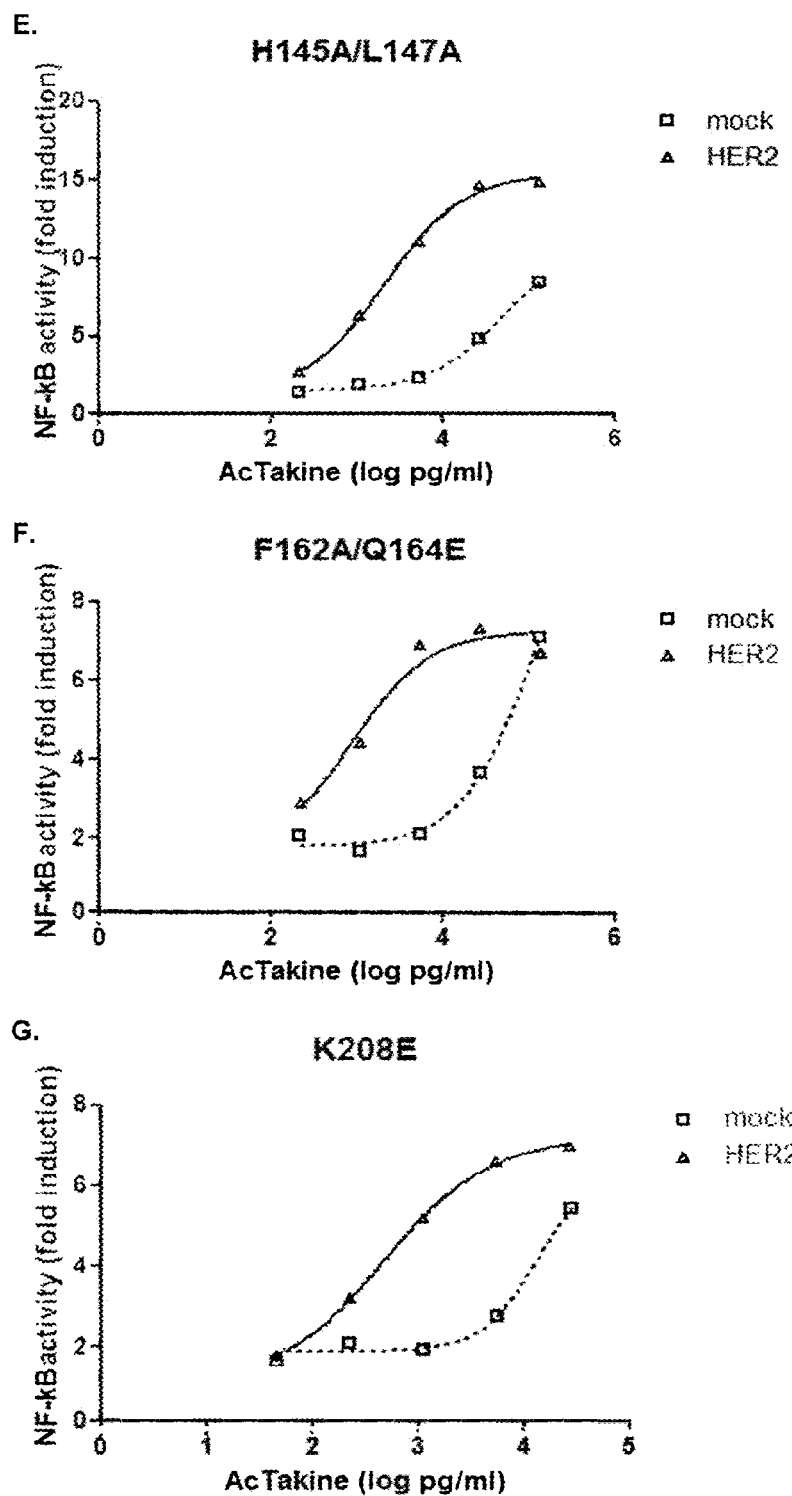

Example 2: IL-1β Activity of Selected Mutant IL-1β-Nanobody Fusions is Restored on Cells Expressing the Nb Targets Wild type IL-1β and 45 IL-1β mutants (Table I) were fused to a well-characterized nanobody recognizing Her2 (1R59B). The IL-1β-nanobody fusion proteins were tested on HEK-Blue™ IL-1β cells, transiently transfected with an NF-κB reportergene plasmid (5 ng/well) and a Her2Δcyt (signalling-deficient) expression plasmid (2 ng/well). Cells were treated for 6 hours with IL-1β-Her2 nanobody fusions (dose response ranging from 0.4 to 250 ng/ml). As demonstrated in FIG. 2A, the IL-1β-Q148G-Her2 nanobody fusion displayed a reduced ability to activate NF-κB as compared to the WT IL1-β-Her2 nanobody fusion. Importantly, targeting of the Q148G mutant to Her2Δcyt-expressing cells restored its activity and produced a dose-response curve for NF-κB activation that perfectly parallels that of the WT IL-1β on mock-transfected cells. Also evident from this figure is a strong targeting effect for the WT IL-1β Her2 nanobody fusion. Similar "activation by targeting" effects were observed for six other IL-1β mutants (R120G, 0131G, H146A, H145A/L147A, F162A/Q164E and K208E) fused to the Her2 nanobody (FIG. 2B).

Figure 3:
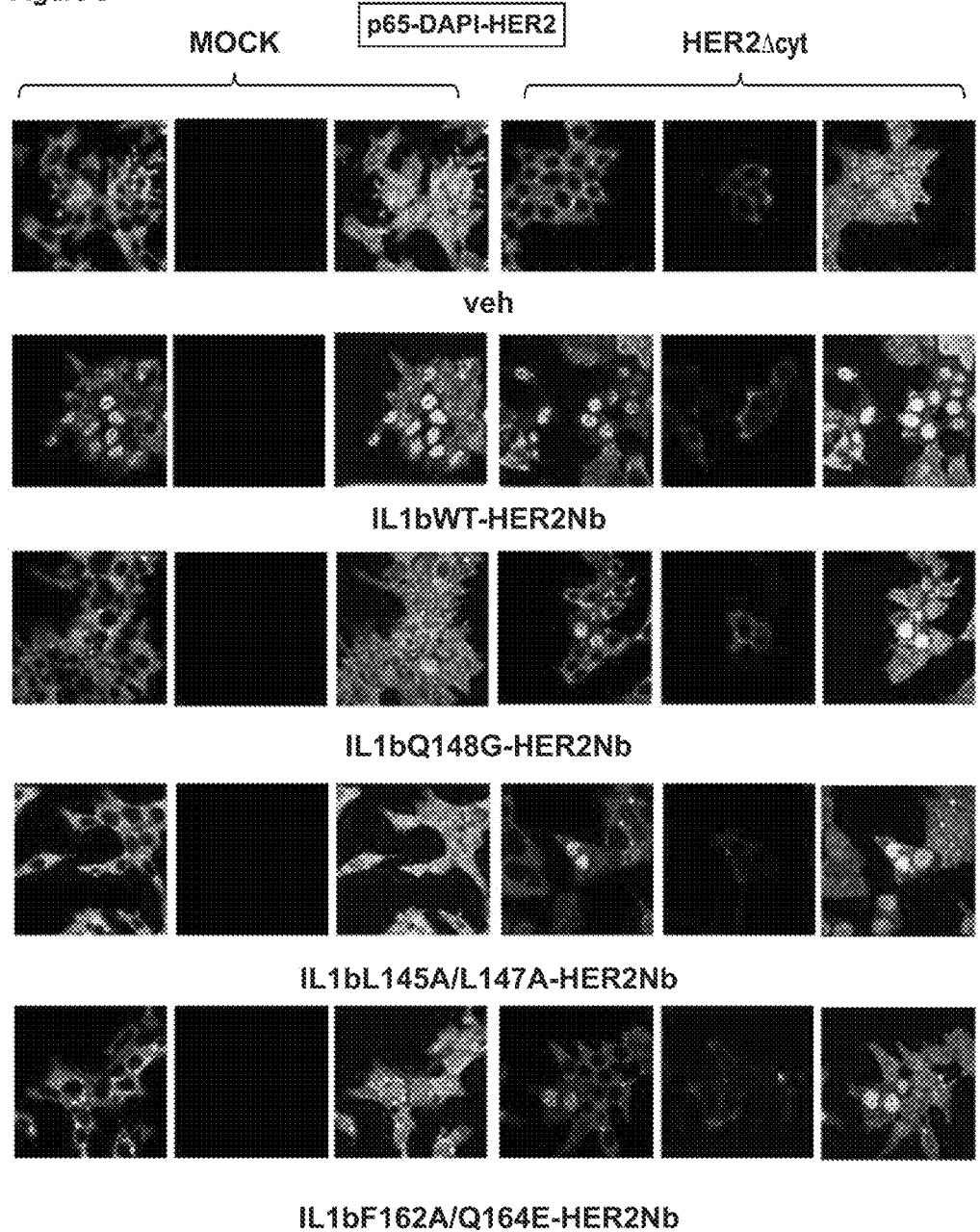
FIG. 3: Effect of wild type and mutant (Q148G, L145A/L147A, F162A/Q164E) IL-1 Her2 nanobody fusions on nuclear translocation of endogenous NF-κB p65 in mock transfected cells, or cells transfected with signaling deficient Her2.

To obtain further proof for the "activation by targeting" concept, we next explored whether we could visualize the selective activation of NF-κB in Her2-expressing cells by the IL-1β-Her2 nanobody fusions via confocal microscopy. We measured activation of endogenous NF-κB by assaying its nuclear translocation. As evident from FIG. 3, only the WT IL-1β-Her2 nanobody fusion promoted translocation of endogenous NF-κB in cells that do not express Her2. Whereas they did not promote detectable NF-κB translocation in mock-transfected cells, the three tested mutant IL1-β-Her2 nanobody fusions triggered NF-κB nuclear translocation in cells that also stained positive for Her2, indicating they only act on targeted cells.

Figure 4:
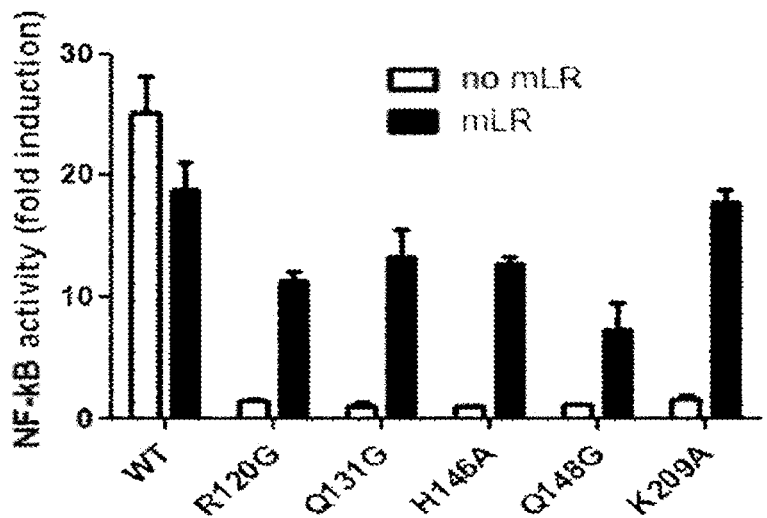
FIG. 4: Induction of the NFκB activity by wild type and 5 different IL-1 mutants, fused to an anti-murine leptin receptor nanobody, on cells expressing the murine leptin receptor (mLR) or not (no mLR).

To evaluate whether the "activation by targeting" concept also works using a nanobody to an unrelated membrane protein, we fused WT IL-1β and five of the disabled IL-1β mutants (R120G, Q131G, H146A, Q148G, K209A) to a previously characterized nanobody recognizing the mLR (4-10). An experiment similar to that reported for the IL-1β-Her2 nanobody fusion (FIGS. 2A-G) was performed using HEK-Blue™ IL-1β cells, transiently transfected with a mLR expression plasmid (10 ng/well). Similar to the results obtained with the Her2 nanobody fusion proteins, all investigated mutant IL-1β nanobody fusions (tested at 12.5 ng/ml) showed a reduced ability, as compared to the WT fusion, to activate NF-κB on cells that do not express mLRs. However, targeting by the mLR nanobody moiety partially restored the activity of the selected mutants (FIG. 4).

Figure 5:
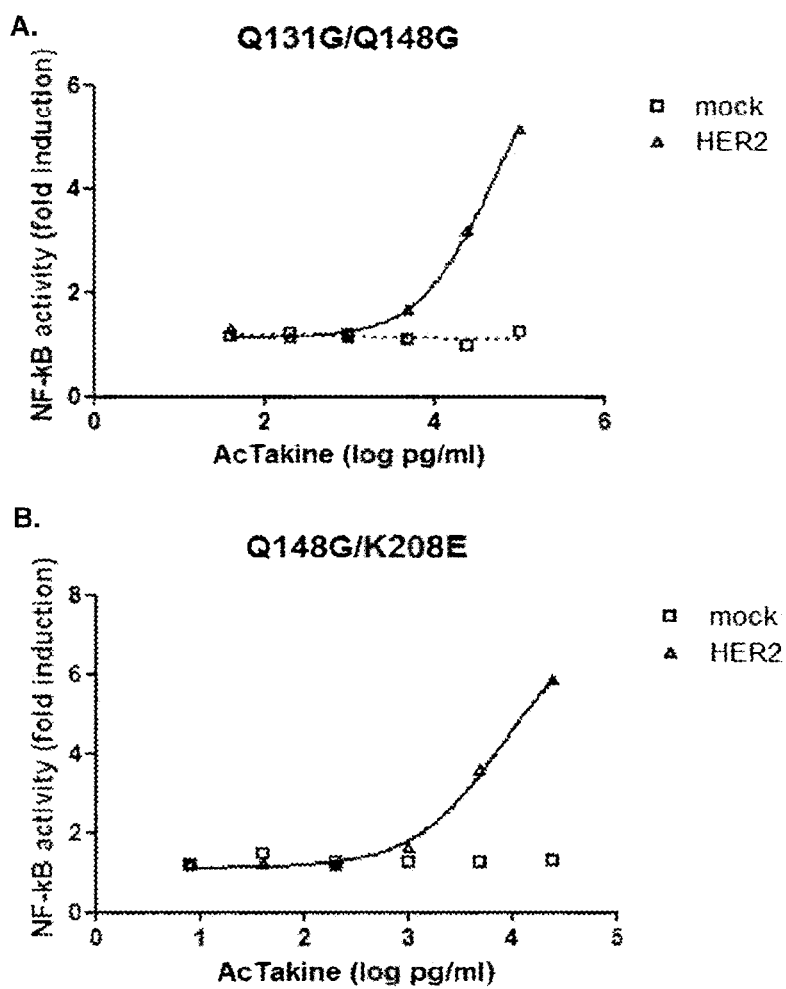
FIGS. 5A-F: Concentration dependency of the induction of the NFκB activity by IL1 double mutants fused to the Her2 nanobody in mock transfected cells, or cells transfected with signaling deficient Her2.
Figure 5:
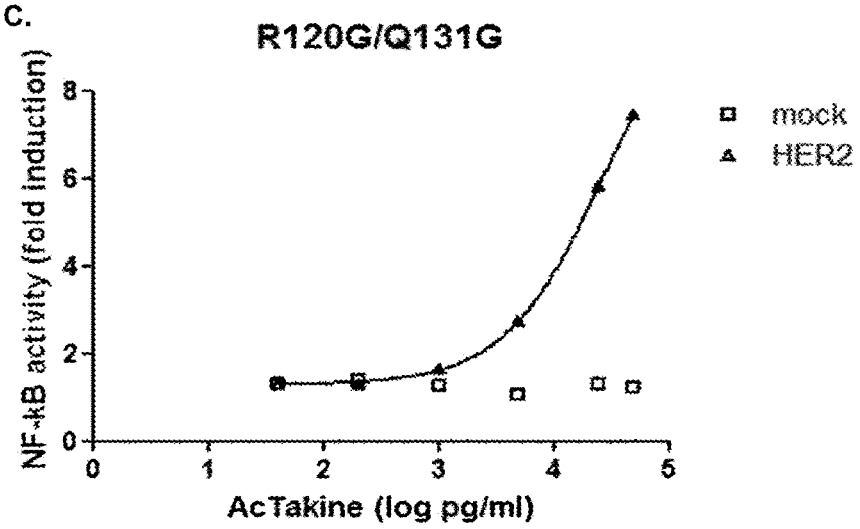
Figure 5:
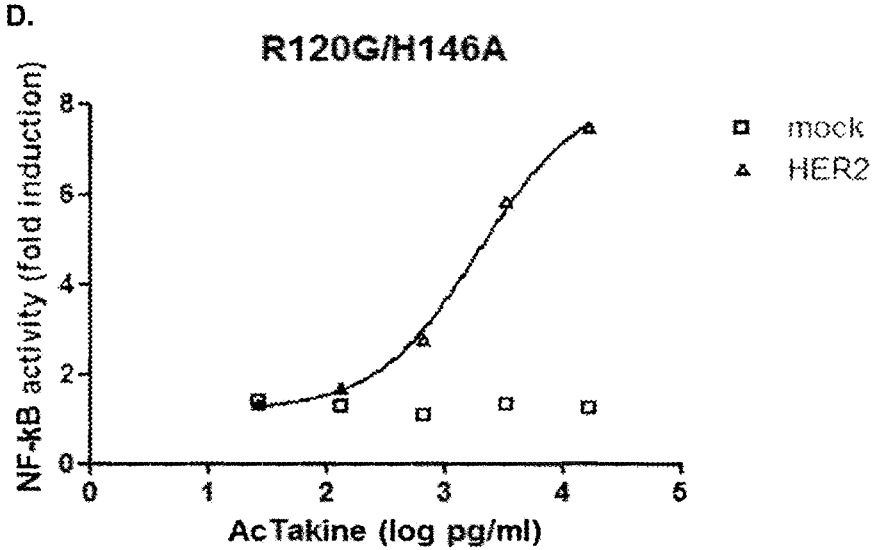
Figure 5:
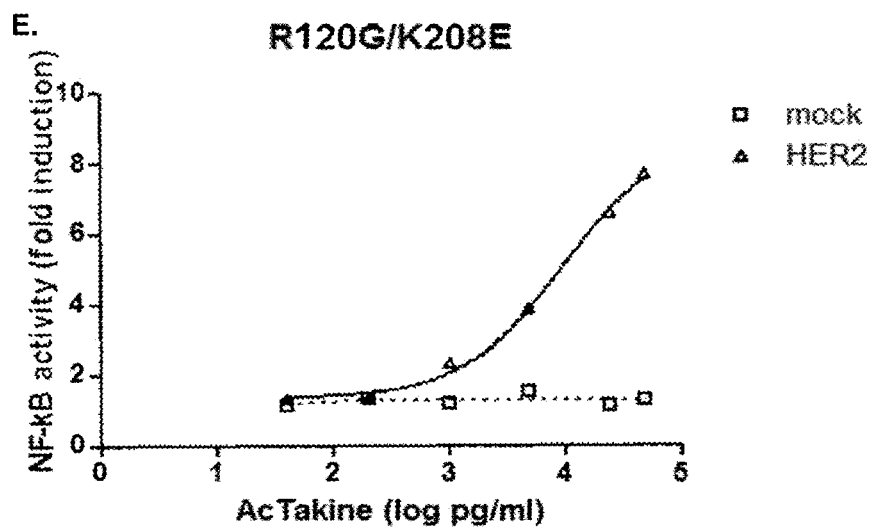
Figure 5:
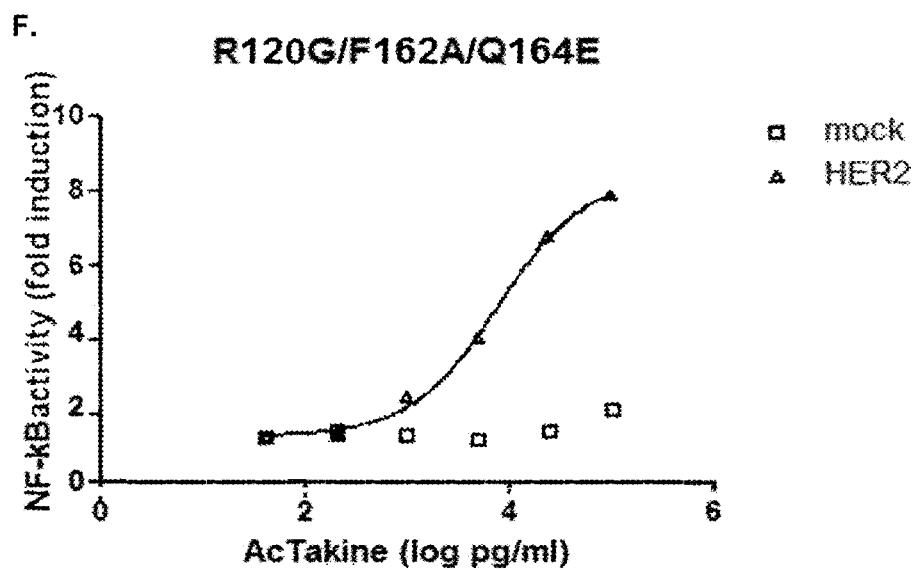

Because the IL-1β mutants described above retained significant residual biological activity, we combined different mutations to obtain double/triple mutants with reduced basal activity. Nine double/triple mutants were tested (cf. table I mutants 46 to 54) and from these, six mutant proteins (Q131G/Q148G, Q148G/K208E, R120G/Q131G, R120G/Q131G, R120G/H146A, R120G/K208E, R120G/F162A/Q164E) displayed no residual activity (using the same assay for measuring NF-κB as in FIGS. 2A-G) on Her2-negative cells, whilst partially restored activity was apparent on cells overexpressing Her2Δcyt (FIGS. 5A-F) (FIG. 5).

These data altogether indicate that targeting partially inactive mutant IL-1β, by fusing it to a nanobody recognizing a cell surface receptor, can restore its activity on nanobody target cells, probably by forced receptor interaction through a membrane concentration effect. The fact that activation by targeting can be accomplished using nanobodies recognizing different classes of membrane proteins indicates broad applicability of the "activation by targeting" concept.

Because these data provide proof of concept for the ability of targeting mutant IL-1 family members to selected cell types, restoring their activity on these target cells only, nanobodies are produced that allow targeting IL-1 family members to physiologically relevant IL-1β target cells. In view of the important role of IL-1 family members as T- and NK-cell activators, the nanobodies are designed to specifically target IL-1 to T- and NK-cell subsets. More specifically nanobodies targeting CCR6, which are predominantly expressed on Th17 cells as well as nanobodies targeting CD8 on cytotoxic T cells are developed and fused to the members of the IL1-family, preferably IL-1β.

Example 3: Effect of IL-1β-Nanobody Fusions on IL-17 Production by Primary Human T Cells Primary human T cells were isolated from buffy coats. First, PBMC's were isolated by lymphoprep density gradient centrifugation and incubated O/N with 0.5 ng/ml rhIL-2 for recovery. Next, T-cells were isolated using the pan-T cell isolation kit (Miltenyi Biotec) according to the manufacturer's instructions. Briefly, T cells were resuspended ($1\times10^6$/ml) in RPMI-1640 supplemented with 10% FCS and CD3/CD28 activating microbeads (Miltenyi Biotec). Next, cells (100 μl/well) were plated in U-bottom 96-well plates and stimulated for 96 hours with the indicated concentrations of IL-1β variants. After an additional 6 hours stimulation with PMA/ionomycin (both at 100 nM), supernatants were recovered and IL-17 levels were determined by Elisa (R&D Systems). Additional cytokines are evaluated via Luminex technology.

For selected mutant IL-1β-nanobody fusions (e.g. with a nanobody targeting CCR6) target cell-specific IL-17 and IFNγ production are evaluated by intracellular staining using a flow cytometric approach.

Also, to corroborate selectivity for the Th17 population, binding to PBMC subpopulations is measured via double staining using the Flag tag and selected CD markers, followed by flow cytometric analysis.

Finally, in a clinically relevant in vitro model of human Th17 cell function, the adjuvant activity of the IL-1β-nanobody fusions is assessed. In view of the need for more efficacious vaccines against *Bordetella pertussis* (or adjuvants for the existing vaccines), we determined whether the selected fusion proteins enhance the human Th17 response in a coculture model of naïve T cells with *B. pertussis*-treated monocyte-derived dendritic cells (MDDCs). Human MDDCs are isolated from buffy coats (using the monocyte isolation kit II, Miltenyi Biotec), treated with different ratios of *B. pertussis* for 48 hours and then cocultured with naïve allogeneic T cells for 12 days. After restimulation with anti-CD3/anti-CD28, the cytokine profiles in supernatants are determined using Elisa/Luminex technology (cfr. supra).

Example 4: Effect of IL-1β-Nanobody Fusions on CTLs

To assess whether IL-1β-CD8 nanobody fusions can specifically enhance the function of CD8+ T cells, human PBMC's are isolated by lymphoprep density gradient centrifugation from buffy coats and stimulated for 24 hours with CD3/CD28 activating microbeads (Miltenyi Biotec) in combination with wt or mutant IL1β-CD8 Nb fusions. The effect of these fusion proteins on CD8+ T cell activation is evaluated by performing intracellular staining for active (phosphorylated) NF-κB and IFNγ. In addition, to investigate whether the IL-1β-nanobody fusions affect CTL degranulation, PBMC's ($2\times10^6$ cells/ml) are differentiated for 48 hours in the presence of phytohaemagglutinin (PHA, 1 μg/ml) and IL-2 (100 IU/ml) in combination with increasing doses of the IL-1β fusion proteins. Next, to induce degranulation, cells are stimulated for 3 hours with CD3/CD28 dynabeads and analysed by flow cytometry. Degranulation is measured via detection of cell surface CD107a, a well-established marker for natural killer activity. In all flow cytometric analyses on leukocyte pools, anti-CD8 staining is included to allow monitoring of the cell-type specificity of the IL-1β-CD8 Nb effects.

Finally to assess whether the IL-1β-CD8 nanobody fusions promote anti-tumor activity in vivo, C57BL/6 mice are injected subcutaneously with TC1 tumor cells, which produce the E6 and E7 antigenic oncoproteins from HPV16. This model was previously used to demonstrate that IL-1β promotes CD8+ T cell-mediated, antigen-specific, anti-tumor responses (Ben-Sasson, 2013). Briefly, mice are immunized four days after tumor injection with a vaccine containing the $HPV16E7_{49-57}$ peptide, combined with DOTAP and LPS, and with our without WT or mutant IL-1β-CD8 Nb fusions or IL-1β-GFP Nb fusions. Tumor size is monitored for 18 days post-immunization.

Example 5: In Vivo Experiments—Vaccine Adjuvans Effect

In a first series of experiments C57BL/6 mice are treated iv/ip with different doses of WT and mutant IL-1β-nanobody fusions and unfused IL-1β, to monitor acute toxicity. Venous blood is collected at different times post treatment by tail venopuncture and the cytokine profile in serum is determined by Luminex assay. In addition, via flow cytometric analysis intracellular cytokine levels (IL-17, IFNγ) and activation of IL-1R (as assessed by measuring phospho-NF-κB levels) are determined in selected leukocyte subsets.

When optimal doses have been established, their adjuvant activity is assessed in a murine vaccination protocol. Briefly, C57BL/6 mice are immunized ip with acellular pertussis vaccine (Pa). The Pa vaccine is composed of 5 μg/mouse of purified recombinant detoxified pertussis toxin (PT9K/129G)+filamentous hemagglutinin (FHA) (composition according to Brereton et al., 2011). 24 hours after immunization, selected mutant IL1β-Nb or PBS are administered ip or iv. Animals are boosted after 28 days. One set of animals is sacrificed 14 days after the second immunization and splenocytes are isolated and restimulated in vitro with medium or FHA for 3 days. Cytokine levels in culture supernatants (IL-17, IFNγ, IL-2, IL-10, IL-5, IL-4, etc.) are determined via Luminex technology. A second set of mice is challenged with *B. pertussis* on day 14 post-boost and sacrificed 2 h and 5 and 10 days post-challenge. Lungs are isolated and CFU in lung homogenates will be quantified on Bordet-Gengou agar plates. Cytokine levels in lung homogenates are determined as in splenocyte supernatants.

In addition, blood is sampled (from the tail vene) before immunization and then every 14 days for determination of *B. pertussis*-specific IgG levels in serum.

Example 6: Direct Antitumor Effect of IL-1β-Nanobody Fusions

To investigate the direct anti-tumour activity of selected IL1-nanobody fusions, we use human A375 melanoma cells, which were shown to be highly susceptible to IL-1-induced cytostatic effects (Morinaga et al., 1990). To allow targeting of mutant IL-1 family members to the A375 cells, a stable A375 clone expressing a cell surface marker to which high-affinity nanobodies are already available (i.e. CD20) is generated. The sensitivity of this cell line, as compared to the parental A375 cells, to the antiproliferative effect of the mutant IL1-nanobody fusion, is investigated in vitro using the XTT proliferation assay. In vivo anti-tumour activity of the mutant IL-1-nanobody fusions is investigated using an A375 xenotransplant model. Briefly, athymic nude mice are inoculated subcutaneously with A375 cells (parental or expressing a surface marker for targeting) and tumor growth is monitored for four weeks in animals treated with PBS or mutant IL1-nanobody fusions.

Example 7: Extension of Principle to IL18: Application in Tumor Models

To assess the indirect anti-tumour activity of IL1 family members, experiments are conducted to address the efficacy of selected mutant IL-18-nanobody fusions using the Meth A syngeneic mouse sarcoma model according to the protocol that was used previously to demonstrate anti-tumour activity of IL-18 (Micallef et al., 1997). IL18 variants used in these experiments consist of mutant IL-18s fused to nanobodies targeting immune cells with tumoricidal properties (i.e. CTLs, NK-cells). The mice are treated with the construct, and a significant reduction of the tumor is noted when compared to the mock treated control.

REFERENCES

Acosta-Rodriguez E V, Napolitani G, Lanzavecchia A, Sallusto F. (2007) Interleukins 1beta and 6 but not transforming growth factor-beta are essential for the differentiation of interleukin 17-producing human T helper cells. Nat Immunol. 8:942-9.

Allakhverdi Z, Smith D E, Comeau M R, Delespesse G. (2007) Cutting edge: The ST2 ligand IL-33 potently activates and drives maturation of human mast cells. J Immunol. 179:2051-4.

Ben-Sasson S Z, Caucheteux S, Crank M, Hu-Li J, Paul W E. (2011) IL-1 acts on T cells to enhance the magnitude of in vivo immune responses. Cytokine.56:122-5.

Ben-Sasson S Z, Hogg A, Hu-Li J, Wingfield P, Chen X, Crank M, Caucheteux S, Ratner-Hurevich M, Berzofsky J A, Nir-Paz R, Paul W E. (2013) IL-1 enhances expansion, effector function, tissue localization, and memory response of antigen-specific CD8 T cells. J Exp Med. 210:491-502.

Blake, A. W., McCartney, L., Flint, J., Bolam, D. N., Boraston, A. B., Gilbert, H. J. and Knox, J. P. (2006) Understanding the biological rationale for the diversity of cellulose-directed carbohydrate-binding molecules in prokaryotic enzymes. J. Biol. Chem. 281, 29321-29329.

Bonilla W V, Fröhlich A, Senn K, Kallert S, Fernandez M, Johnson S, Kreutzfeldt M, Hegazy A N, Schrick C, Fallon P G, Klemenz R, Nakae S, Adler H, Merkler D, Lohning M, Pinschewer D D. (2012). The alarmin interleukin-33 drives protective antiviral CD8+ T cell responses. Science. 335:984-9.

Brecht A., Gauglitz G., Polster J. (1993). Interferometric immunoassay in a FIA-system—A sensitive and rapid approach in label-free immunosensing., Biosens Bioelectron 8:387-392.

Brereton C F, Sutton C E, Ross P J, Iwakura Y, Pizza M, Rappuoli R, Lavelle E C, Mills K H. (2011). Escherichia coli heat-labile enterotoxin promotes protective Th17 responses against infection by driving innate IL-1 and IL-23 production. J Immunol. 2011 May 15; 186(10): 5896-906.

Dimitrov, D. S. (2009) Engineered CH2 domains (nanoantibodies). mAbs 1, 26-28.

Dinarello C A, Simon A, van der Meer J W. (2012). Treating inflammation by blocking interleukin-1 in a broad spectrum of diseases. Nat Rev Drug Discov. 11:633-52.

Dunne A, Ross P J, Pospisilova E, Masin J, Meaney A, Sutton C E, Iwakura Y, Tschopp J, Sebo P, Mills K H. (2010). Inflammasome activation by adenylate cyclase toxin directs Th17 responses and protection against Bordetella pertussis. J Immunol. 185:1711-9.

Higgins S C, Jarnicki A G, Lavelle E C, Mills K H. TLR4 mediates vaccine-induced protective cellular immunity to Bordetella pertussis: role of IL-17-producing T cells. J Immunol. 2006 Dec. 1; 177(11):7980-9.

Khader S A, Bell G K, Pearl J E, Fountain J J, Rangel-Moreno J, Cilley G E, Shen F, Eaton S M, Gaffen S L, Swain S L, Locksley R M, Haynes L, Randall T D, Cooper A M. (2007). IL-23 and IL-17 in the establishment of protective pulmonary CD4+ T cell responses after vaccination and during Mycobacterium tuberculosis challenge. Nat Immunol. 2007 8:369-77.

Killar, L M., Hatfield, C. A., Carding, S. R., Pan, M., Winterrowd, G. E. and Bottomly, K. (1989) In vivo administration of interleukin 1 elecits an increased Ia antigen expression on B cells throught the production of interleukin 4. Eur. J. Immunol. 19, 2205-2210.

Kinoshita, M., Miyazaki, H., Ono, S., Inatsu, A., Nakashima, H., Tsujimoto, H., Shinomiya, N., Saitoh, D. and Seki, S. (2011). Enhancement of neutrophil function by interleukin 18 therapy protects burn-injuredf mice from methicillin-resistant Staphylococcus aureus. Infect. Immun. 79, 2670-2680.

Kolmar, H. (2008) Alternative binding proteins: biological activity and therapeutic potential of cysteine-knot miniproteins. FEBS J. 275, 2684-2690.

Leung B P, Culshaw S, Gracie J A, Hunter D, Canetti C A, Campbell C, Cunha F, Liew F Y, McInnes I B. (2001). A role for IL-18 in neutrophil activation. J Immunol. 167: 2879-86.

Loeffler M, Le'Negrate G, Krajewska M, Reed J C. (2008). IL-18-producing Salmonella inhibit tumor growth. Cancer Gene Ther. 15:787-94.

Micallef M J, Tanimoto T, Kohno K, Ikeda M, Kurimoto M. (1997). Interleukin 18 induces the sequential activation of natural killer cells and cytotoxic T lymphocytes to protect syngeneic mice from transplantation with Meth A sarcoma. Cancer Res.; 57:4557-63.

Morinaga Y, Hayashi H, Takeuchi A, Onozaki K. (1990). Antiproliferative effect of interleukin 1 (IL-1) on tumor cells: G0-G1 arrest of a human melanoma cell line by IL-1. Biochem Biophys Res Commun. 173:186-92.

Nygren, P-A. (2008) Alternative binding proteins: affibody binding proteins developed from a small three-helix bundle scaffold. FEBS J. 275, 2668-2676.

Okamura H, Tsutsi H, Komatsu T, Yutsudo M, Hakura A, Tanimoto T, Torigoe K, Okura T, Nukada Y, Hattori K, et al. (1995). Cloning of a new cytokine that induces IFN-gamma production by T cells. Nature. 378:88-91.

Rangnekar V V, Waheed S, Rangnekar V M. (1992). Interleukin-1-inducible tumor growth arrest is characterized by activation of cell type-specific "early" gene expression programs. J Biol Chem. 267:6240-8.

Robertson M J, Kirkwood J M, Logan T F, Koch K M, Kathman S, Kirby L C, Bell W N, Thurmond L M, Weisenbach J, Dar M M. (2008). A dose-escalation study of recombinant human interleukin-18 using two different schedules of administration in patients with cancer. Clin Cancer Res. 14:3462-9

Scatchard G. (1949). Ann New York Acad Sci 51, 660-72.

Schmitz J, Owyang A, Oldham E, Song Y, Murphy E, McClanahan T K, Zurawski G, Moshrefi M, Qin J, Li X, Gorman D M, Bazan J F, Kastelein R A. (2005). IL-33, an interleukin-1-like cytokine that signals via the IL-1 receptor-related protein ST2 and induces T helper type 2-associated cytokines. Immunity. 23:479-90.

Shaw M H, Kamada N, Kim Y G, Núñez G. (2012). Microbiota-induced IL-1β, but not IL-6, is critical for the development of steady-state TH17 cells in the intestine. J Exp Med. 209:251-8.

Sims J E, Smith D E. The IL-1 family: regulators of immunity. (2010). Nat Rev Immunol. 10:89-102.

Skerra, A. (2008) Alternative binding proteins: anticalins—harnessing the structural plasticity of the lipocalin ligand pocket to engineer novel binding activities. FEBS J. 275, 2677-2683.

Stump, M. T., Binz, H. K., Amstutz, P. (2008) DARPins: a new generation of protein therapeutics. Drug iscov. Today 13, 695-701.

Sutton C, Brereton C, Keogh B, Mills K H, Lavelle E C. (2006). A crucial role for interleukin (IL)-1 in the induction of IL-17-producing T cells that mediate autoimmune encephalomyelitis. J Exp Med. 203:1685-91.

Takeda K, Tsutsui H, Yoshimoto T, Adachi O, Yoshida N, Kishimoto T, Okamura H, Nakanishi K, Akira S. (1998). Defective NK cell activity and Th1 response in IL-18-deficient mice. Immunity. 8:383-90.

Tramontano, A., Bianchi, E., Venturini, S., Martin, F., Pessi, A and Sollazzo, M. (1994) The making of the minibody: an engineered beta-protein for the display of conformationally constrained peptides. J. Mol. Recognition 7, 9-24.

Usui N, Mimnaugh E G, Sinha B K. (1991). A role for the interleukin 1 receptor in the synergistic antitumor effects of human interleukin 1 alpha and etoposide against human melanoma cells. Cancer Res. 1991 51:769-74.

Vanden Berghe W, Plaisance S, Boone E, De Bosscher K, Schmitz M L, Fiers W, Haegeman G. (1998). p38 and extracellular signal-regulated kinase mitogen-activated protein kinase pathways are required for nuclear factor-kappaB p65 transactivation mediated by tumor necrosis factor. J Biol Chem. 273:3285-90.

Vaneycken I, Devoogdt N, Van Gassen N, Vincke C, Xavier C, Wernery U, Muyldermans S, Lahoutte T, Caveliers V. (2011). Preclinical screening of anti-HER2 nanobodies for molecular imaging of breast cancer. FASEB J. 25:2433-46.

Wigginton J M, Lee J K, Wiltrout T A, Alvord W G, Hixon J A, Subleski J, Back T C, Wiltrout R H. (2002). Synergistic engagement of an ineffective endogenous antitumor immune response and induction of IFN-gamma and Fas-ligand-dependent tumor eradication by combined administration of IL-18 and IL-2. J Immunol. 169:4467-74.

Wilke C M, Bishop K, Fox D, Zou W. (2011). Deciphering the role of Th17 cells in human disease. Trends Immunol. 32:603-11.

Ye P, Rodriguez F H, Kanaly S, Stocking K L, Schurr J, Schwarzenberger P, Oliver P, Huang W, Zhang P, Zhang J, Shellito J E, Bagby G J, Nelson S, Charrier K, Peschon J J, Kolls J K. (2001). Requirement of interleukin 17 receptor signaling for lung CXC chemokine and granulocyte colony-stimulating factor expression, neutrophil recruitment, and host defense. J Exp Med. 194:519-27.

Zabeau L, Verhee A, Catteeuw D, Faes L, Seeuws S, Decruy T, Elewaut D, Peelman F, Tavernier J. (2012). Selection of non-competitive leptin antagonists using a random nanobody-based approach. Biochem J. 441:425-34.

Zaki M H, Vogel P, Body-Malapel M, Lamkanfi M, Kanneganti T D. (2010). IL-18 production downstream of the NIrp3 inflammasome confers protection against colorectal tumor formation. J Immunol. 185:4912-20.

The invention claimed is:

1. A composition comprising a fusion protein comprising:
   (1) a mutated human IL-1β cytokine characterized by a reduced activity as compared to wild type human IL-1β cytokine, wherein the mutation is one or more mutations selected from R120G, Q131G, L145A, H146A, L147A, Q148G, F162A, Q164E, and K208E, wherein the numbering is based on the human IL-1β sequence, and
   (2) a targeting moiety comprising a variable domain of camelid heavy chain antibodies (VHH), wherein the targeting moiety restores activity of the mutated human IL-1β cytokine on target cells.

2. The composition according to claim 1, wherein said targeting moiety is directed to a marker expressed on human IL-1β cytokine receptor expressing cell.

3. The composition according to claim 2, wherein said targeting moiety is directed to a marker expressed on an IL-1R1 and/or IL-1RacP expressing cell.

4. The composition according to claim 1, wherein the mutated human IL-1β cytokine is characterized by a reduced affinity for its receptor as compared to a wild type human IL-1β cytokine.

5. The composition according to claim 1, wherein said targeting moiety is directed to a tissue specific marker.

6. The composition according to claim 1, wherein said targeting moiety is directed to Her2 or leptin receptor.

7. The composition according to claim 1, wherein the mutated human IL-1β further comprises at least one mutation selected from the group consisting of A117G/P118G, L122A, T125G/L126G, R127G, K132A, S137G/Q138Y, Q148G/Q150G, Q150G/D151A, M152G, F162A/Q164E, F166A, Q164E/E167K, N169G/D170G, I172A, V174A, K209A, K209A/K210A, E221K, E221S/N224A, N224S/K225S, E244K and N245Q.

8. The composition according to claim 1, wherein the mutated human IL-1β comprises Q131G and Q148G.

9. The composition according to claim 8, wherein the targeting moiety comprises a VHH against HER2 or leptin receptor.

10. The composition according to claim 1, wherein the mutated human IL-1β comprises Q148G and K208E.

11. The composition according to claim 10, wherein the targeting moiety comprises a VHH against HER2 or leptin receptor.

12. The composition according to claim 1, wherein the mutated human IL-1β comprises R120G and Q131G.

13. The composition according to claim 12, wherein the targeting moiety comprises a VHH against HER2 or leptin receptor.

14. The composition according to claim 1, wherein the mutated human IL-1β comprises R120G and H146A.

15. The composition according to claim 14, wherein the targeting moiety comprises a VHH against HER2 or leptin receptor.

16. The composition according to claim 1, wherein the mutated human IL-1β comprises R120G and K208E.

17. The composition according to claim 16, wherein the targeting moiety comprises a VHH against HER2 or leptin receptor.

18. The composition according to claim 1, wherein the mutated human IL-1β comprises R120G, F162A, and Q164E.

19. The composition according to claim 18, wherein the targeting moiety comprises a VHH against HER2 or leptin receptor.

* * * * *